US011564823B2

(12) United States Patent
Brookover et al.

(10) Patent No.: US 11,564,823 B2
(45) Date of Patent: Jan. 31, 2023

(54) VERSATILE ORTHOPEDIC DEVICE

(71) Applicant: OSSUR HF, Reykjavik (IS)

(72) Inventors: Derek Brookover, Foothill Ranch, CA (US); Jared Olivo, Foothill Ranch, CA (US)

(73) Assignee: OSSUR HF, Reykjavik (IS)

( * ) Notice: Subject to any disclaimer, the term of this patent is extended or adjusted under 35 U.S.C. 154(b) by 294 days.

(21) Appl. No.: 16/801,582

(22) Filed: Feb. 26, 2020

(65) Prior Publication Data
US 2020/0188157 A1 Jun. 18, 2020

Related U.S. Application Data

(63) Continuation of application No. 14/793,230, filed on Jul. 7, 2015, now Pat. No. 10,588,770.

(60) Provisional application No. 62/097,206, filed on Dec. 29, 2014, provisional application No. 62/060,757, filed on Oct. 7, 2014, provisional application No. 62/023,148, filed on Jul. 10, 2014.

(51) Int. Cl.
*A61F 5/01* (2006.01)

(52) U.S. Cl.
CPC .......... *A61F 5/0123* (2013.01); *A61F 5/0125* (2013.01); *A61F 2005/0137* (2013.01); *A61F 2005/0139* (2013.01); *A61F 2005/0144* (2013.01)

(58) Field of Classification Search
CPC .................. A61F 5/0123; A61F 5/0125; A61F 2005/0137; A61F 2005/0139; A61F 2005/0144
See application file for complete search history.

(56) References Cited

U.S. PATENT DOCUMENTS

| 689,991 A | 12/1901 | Rubin |
| 828,573 A | 8/1906 | Rubin |
| 1,153,334 A | 9/1915 | Oswald |
| 2,615,218 A | 10/1952 | Ross |
| 2,636,234 A | 4/1953 | Reiter |
| 3,575,166 A | 4/1971 | Rosman et al. |
| 3,596,288 A | 8/1971 | Marchello |

(Continued)

FOREIGN PATENT DOCUMENTS

| EP | 2679203 A1 | 1/2014 |
| EP | 2904992 A3 | 11/2015 |

(Continued)

OTHER PUBLICATIONS

International Search Report from corresponding International PCT Application No. PCT/US2015/039356, dated Sep. 30, 2015.

(Continued)

*Primary Examiner* — Camtu T Nguyen
(74) *Attorney, Agent, or Firm* — Workman Nydegger

(57) ABSTRACT

A versatile orthopedic device is arranged to convert between ligament and osteoarthritis treatment, and to accommodate a variety of leg anatomies. The orthopedic device is preferably configured as a double-upright brace indicating struts, frame component sections and associated hinges preferably intended to be along both medial and lateral sides of a wearer's leg. A strap kit with an unloading strap system may be added to the orthopedic device for conversion into an orthopedic device for osteoarthritis relief.

19 Claims, 11 Drawing Sheets

(56) References Cited

U.S. PATENT DOCUMENTS

| | | | |
|---|---|---|---|
| 3,669,105 A | 6/1972 | Castiglia | |
| 3,853,071 A | 12/1974 | Snyder et al. | |
| 4,064,874 A | 12/1977 | Valin | |
| 4,241,730 A | 12/1980 | Helfet | |
| 4,271,999 A | 6/1981 | Stravitz | |
| D284,702 S | 7/1986 | Castillo | |
| 4,660,240 A | 4/1987 | Hutton et al. | |
| 4,732,143 A | 3/1988 | Kausek et al. | |
| 4,738,341 A | 4/1988 | Asano | |
| 4,838,251 A | 6/1989 | Chignon et al. | |
| 4,854,308 A | 8/1989 | Drillio | |
| 4,856,501 A | 8/1989 | Castillo et al. | |
| 4,991,571 A | 2/1991 | Kausek | |
| 4,993,127 A | 2/1991 | Mechem et al. | |
| 5,022,391 A | 6/1991 | Weidenburner | |
| 5,131,385 A | 7/1992 | Kuehnegger et al. | |
| 5,230,697 A | 7/1993 | Castillo et al. | |
| 5,277,698 A | 1/1994 | Taylor | |
| 5,288,286 A | 2/1994 | Davis et al. | |
| D346,028 S | 4/1994 | Lengyel | |
| 5,311,972 A | 5/1994 | Plath | |
| 5,336,161 A | 8/1994 | Lengyel | |
| D357,070 S | 4/1995 | Castillo | |
| 5,415,625 A | 5/1995 | Cassford et al. | |
| D359,710 S | 6/1995 | Chinni et al. | |
| 5,458,565 A | 10/1995 | Tillinghast, III et al. | |
| 5,519,896 A | 5/1996 | Ford | |
| D372,983 S | 8/1996 | Nebolon | |
| 5,562,605 A * | 10/1996 | Taylor | A41D 13/0568 602/26 |
| 5,571,078 A | 11/1996 | Malewicz | |
| 5,577,998 A | 11/1996 | Johnson, Jr. et al. | |
| 5,586,970 A | 12/1996 | Morris et al. | |
| 5,743,865 A | 4/1998 | Townsend | |
| 5,766,140 A | 6/1998 | Tillinghast, III et al. | |
| 5,782,780 A | 7/1998 | Mason et al. | |
| 5,807,294 A | 9/1998 | Cawley et al. | |
| 5,891,071 A | 4/1999 | Stearns et al. | |
| 6,056,713 A | 5/2000 | Hayashi | |
| 6,155,998 A | 12/2000 | Gilmour | |
| D435,807 S | 1/2001 | Anscher | |
| RE37,297 E | 7/2001 | Smith, III | |
| 6,290,664 B1 | 9/2001 | Nauert | |
| 6,361,515 B1 | 3/2002 | Gilmour | |
| 6,425,166 B1 | 7/2002 | Seligman et al. | |
| 6,461,318 B2 | 10/2002 | Freeman et al. | |
| 6,623,439 B2 | 9/2003 | Nelson et al. | |
| 6,687,963 B1 | 2/2004 | Chang | |
| 6,702,770 B2 | 3/2004 | Bremer et al. | |
| 6,719,713 B2 | 4/2004 | Mason | |
| 6,740,054 B2 | 5/2004 | Stearns | |
| 6,793,641 B2 | 9/2004 | Freeman et al. | |
| 6,796,952 B2 | 9/2004 | Nelson et al. | |
| 6,866,646 B2 | 3/2005 | Hopkins et al. | |
| 6,875,187 B2 | 4/2005 | Castillo | |
| 6,878,126 B2 | 4/2005 | Nelson et al. | |
| 6,890,314 B2 | 5/2005 | Seligman | |
| 6,936,019 B2 | 8/2005 | Mason | |
| 6,962,571 B2 | 11/2005 | Castillo | |
| 6,978,523 B2 | 12/2005 | Downing et al. | |
| 7,045,694 B2 | 5/2006 | Yasunori | |
| 7,059,329 B2 | 6/2006 | Mason et al. | |
| 7,120,982 B2 | 10/2006 | Downing et al. | |
| 7,125,392 B2 | 10/2006 | Scott | |
| 7,198,610 B2 | 4/2007 | Ingimundarson et al. | |
| 7,201,728 B2 | 4/2007 | Sterling | |
| 7,204,819 B2 | 4/2007 | Berger | |
| 7,207,960 B2 | 4/2007 | Kenney | |
| 7,231,698 B2 | 6/2007 | Downing et al. | |
| 7,261,700 B2 | 8/2007 | Verkade | |
| 7,285,103 B2 | 10/2007 | Nathanson | |
| 7,311,687 B2 | 12/2007 | Hoffmeier et al. | |
| D565,461 S | 4/2008 | Johnson et al. | |
| 7,426,773 B2 | 9/2008 | Downing et al. | |
| 7,431,708 B2 | 10/2008 | Sreeramagiri | |
| D581,314 S | 11/2008 | Janz | |
| D581,315 S | 11/2008 | Paris et al. | |
| 7,462,160 B2 | 12/2008 | Nobbe et al. | |
| 7,479,122 B2 | 1/2009 | Ceriani et al. | |
| 7,534,219 B2 | 5/2009 | Stearns | |
| 7,562,422 B2 | 7/2009 | D'Addario et al. | |
| 7,597,675 B2 | 10/2009 | Ingimundarson et al. | |
| 7,601,131 B2 | 10/2009 | Gilmour | |
| 7,608,051 B1 | 10/2009 | Nace | |
| 7,749,183 B2 | 7/2010 | Ingimundarson et al. | |
| D627,073 S | 11/2010 | Nace | |
| 7,918,812 B2 | 4/2011 | Knecht | |
| 7,935,068 B2 | 5/2011 | Einarsson | |
| 7,959,589 B2 | 6/2011 | Sreeramagiri et al. | |
| D647,622 S | 10/2011 | Lee et al. | |
| 8,043,243 B2 | 10/2011 | Nathanson et al. | |
| 8,048,013 B2 | 11/2011 | Ingimundarson et al. | |
| 8,282,588 B2 | 10/2012 | Ingimundarson et al. | |
| 8,585,623 B2 | 11/2013 | Ingimundarson | |
| 8,740,829 B2 | 6/2014 | Lee et al. | |
| 2002/0072695 A1 | 6/2002 | Doty et al. | |
| 2002/0103449 A1 | 8/2002 | Freeman et al. | |
| 2003/0045822 A1 | 3/2003 | Nelson et al. | |
| 2003/0045823 A1 | 3/2003 | Nelson et al. | |
| 2003/0144620 A1 | 7/2003 | Sieller et al. | |
| 2004/0097859 A1 | 5/2004 | Stearns | |
| 2004/0133139 A1 | 7/2004 | Nelson et al. | |
| 2004/0204667 A2 | 10/2004 | Nelson et al. | |
| 2005/0192523 A1 | 9/2005 | Knecht et al. | |
| 2006/0004311 A1 | 1/2006 | Hargrave et al. | |
| 2006/0084899 A1 | 4/2006 | Verkade et al. | |
| 2006/0129075 A1 | 6/2006 | Scheinberg et al. | |
| 2006/0135901 A1 | 6/2006 | Ingimundarson et al. | |
| 2006/0155232 A1 | 7/2006 | Ceriani | |
| 2006/0162135 A1 | 7/2006 | Howell et al. | |
| 2006/0167394 A1 | 7/2006 | Ceriani et al. | |
| 2006/0230583 A1 | 10/2006 | Chen | |
| 2006/0247565 A1 | 11/2006 | Cormier et al. | |
| 2007/0197946 A1 | 8/2007 | Gilmour | |
| 2007/0244419 A1 | 10/2007 | Mason et al. | |
| 2008/0195013 A1 | 8/2008 | Ingimundarson et al. | |
| 2008/0195014 A1 | 8/2008 | Ingimundarson et al. | |
| 2008/0195015 A1 | 8/2008 | Ingimundarson et al. | |
| 2008/0208085 A1 | 8/2008 | Nan | |
| 2008/0208095 A1 | 8/2008 | Kazmierczak et al. | |
| 2008/0237250 A1 | 10/2008 | Swansey | |
| 2008/0294082 A1 | 11/2008 | Chang et al. | |
| 2009/0070969 A1 | 3/2009 | Fildan et al. | |
| 2009/0124948 A1 | 5/2009 | Ingimundarson et al. | |
| 2009/0287127 A1 | 11/2009 | Hu et al. | |
| 2010/0323859 A1 | 12/2010 | Von Hoffmann et al. | |
| 2011/0082402 A1 | 4/2011 | Oddou et al. | |
| 2012/0046585 A1 | 2/2012 | Lee et al. | |
| 2012/0059296 A1 | 3/2012 | Kompa | |
| 2012/0089064 A1 | 4/2012 | Chang | |
| 2012/0271211 A1 | 10/2012 | Bledsoe | |
| 2013/0144197 A1 | 6/2013 | Ingimundarson et al. | |
| 2013/0184628 A1 | 7/2013 | Ingimundarson et al. | |
| 2013/0253394 A1 | 9/2013 | Romo | |
| 2013/0331751 A1 | 12/2013 | Lee et al. | |
| 2014/0124557 A1 | 5/2014 | Velarde | |
| 2014/0130333 A1* | 5/2014 | Jonsson | A44B 18/0073 29/525.01 |
| 2014/0221891 A1* | 8/2014 | Sreeramagiri | A61F 5/0123 602/16 |
| 2014/0323937 A1 | 10/2014 | Knecht | |
| 2019/0105189 A1* | 4/2019 | Petursson | A61F 5/0123 |

FOREIGN PATENT DOCUMENTS

| | | |
|---|---|---|
| FR | 2862205 A1 | 5/2005 |
| WO | 01/89434 A1 | 11/2001 |
| WO | 03/065942 A1 | 8/2003 |

(56) References Cited

FOREIGN PATENT DOCUMENTS

WO   2008/061300 A1   5/2008
WO   2010/088716 A1   8/2010

OTHER PUBLICATIONS

Dj Orthopedics Product Information Sheet for Defiance, obtained prior to Aug. 20, 2010, 1 page, www.djortho.com.
Orthofix Sports Medicine Product Information Sheet for BREG New! Fusion XT With Air Tech Innovation, obtained prior to Aug. 20, 2010, 1 page.
OSSUR Product Information Sheet for CTi OTS, obtained prior to Aug. 20, 2010, 1 page, www.ossur.com.
OSSUR Product Information Sheet for PARADIGM/Custom, obtained prior to Aug. 20, 2010, 1 page, www.ossur.com.
OSSUR Product Information Sheet for CTi Custom (color), obtained prior to Aug. 20, 2010, 1 page, www.ossur.com.
OSSUR Product Information Sheet for The Total Support System, obtained prior to Aug. 20, 2010, 1 page.
OSSUR Product Catalog for OASYS/OTS, obtained from URL: http://assets.ossur.com/library/15876/OrthoCatalog09%2019.pdf, 1 page, Jun. 30, 2015.
OSSUR Product Information Sheet for The MVP Contour Brace, obtained from URL: http://assets.ossur.com/library/23213/MVP%20Ligament%20Brochure%20Page.pdf, 2 pages, Jun. 30, 2015.

* cited by examiner

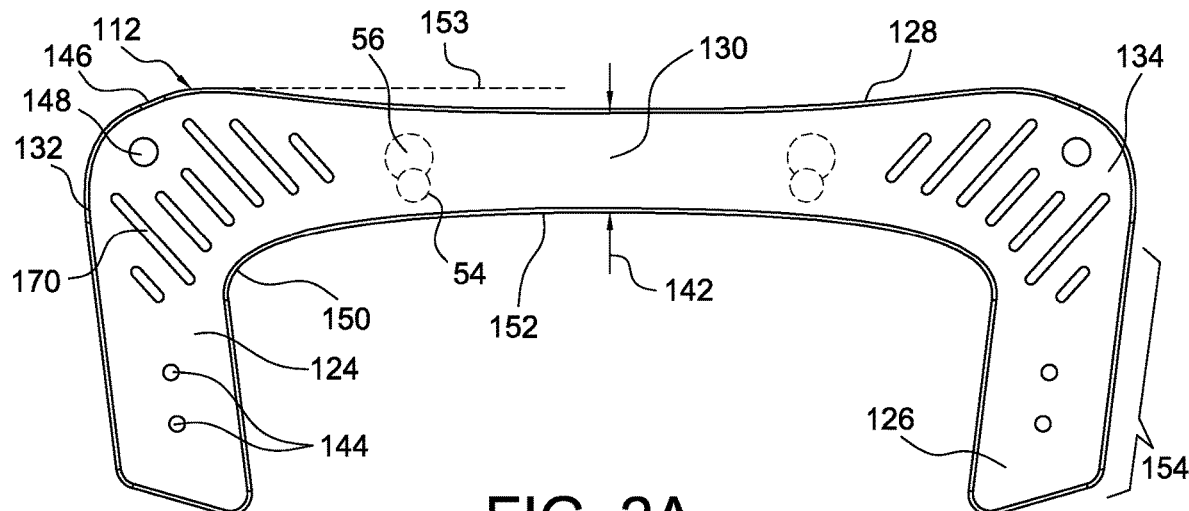
FIG. 2A
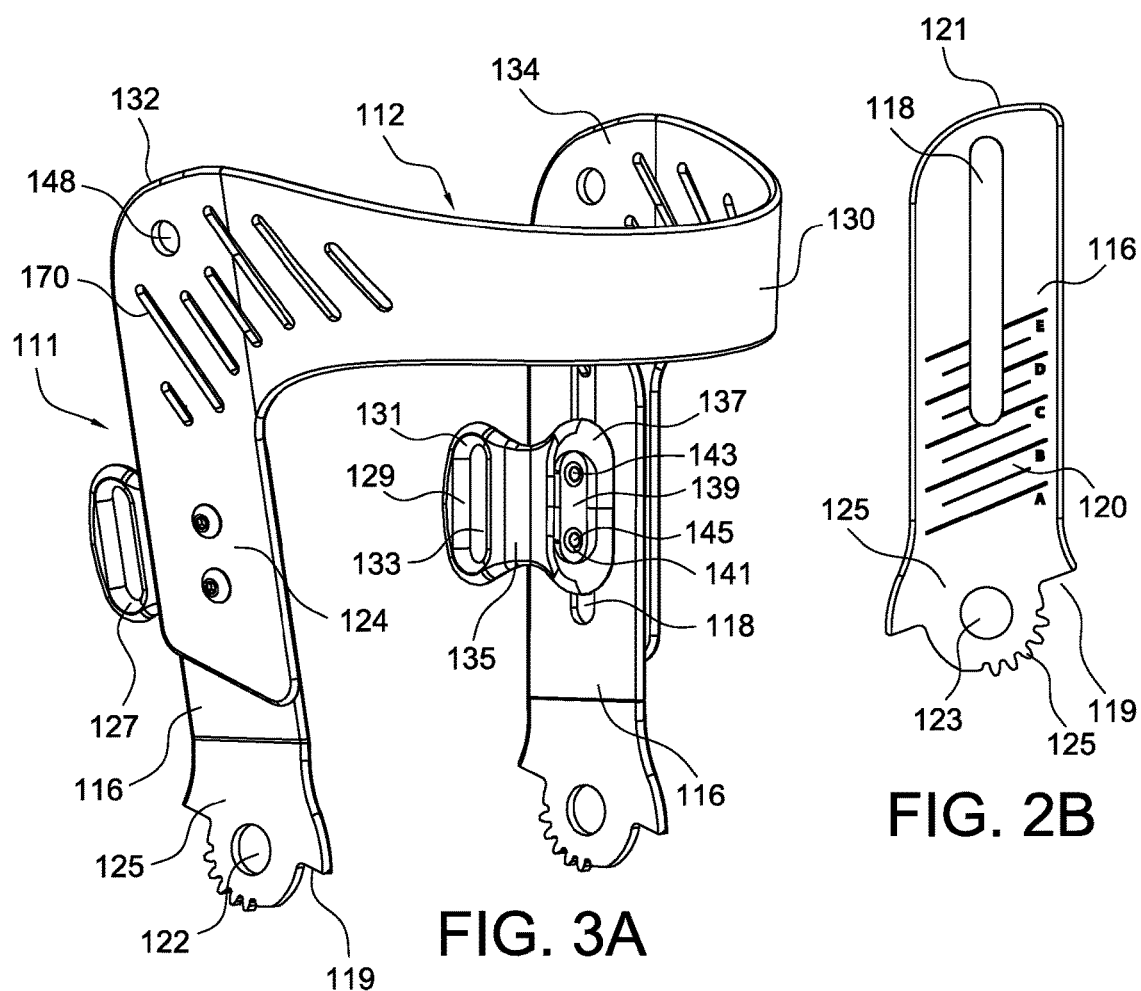
FIG. 2B
FIG. 3A

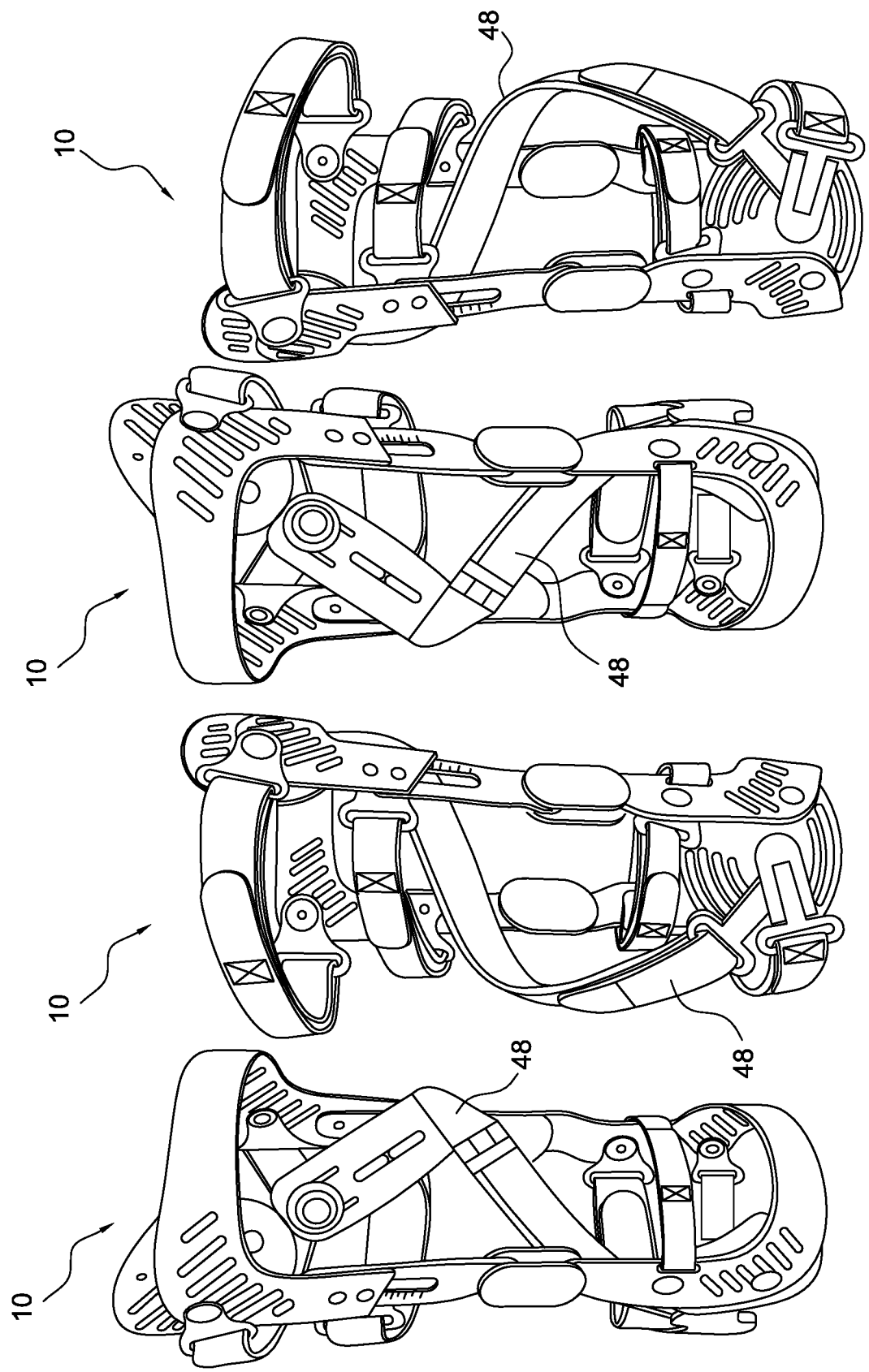

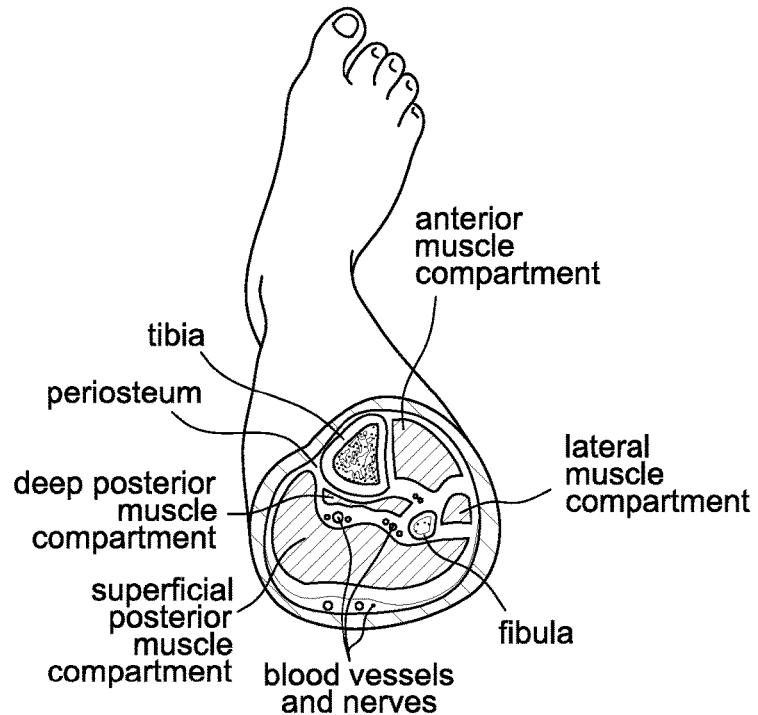
FIG. 9
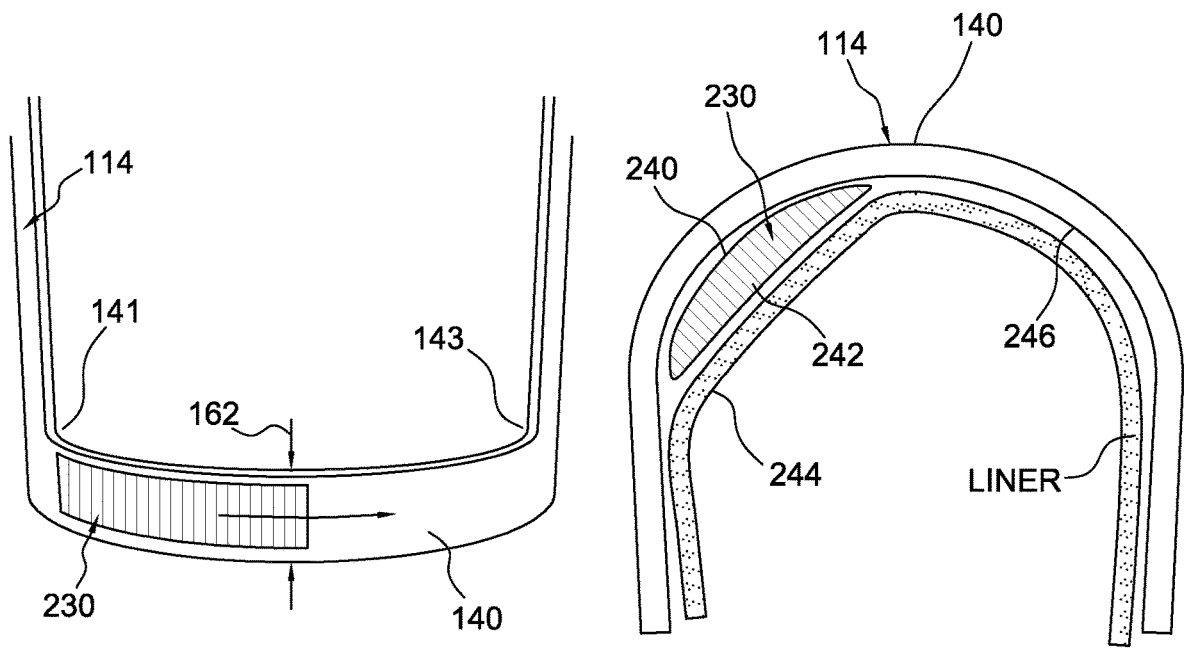
FIG. 10
FIG. 11

VERSATILE ORTHOPEDIC DEVICE

FIELD OF THE DISCLOSURE

The disclosure relates to a versatile orthopedic device, and more specifically to a knee brace arranged in a streamline and efficient manner for a ligament user, and configured to be converted to a knee brace for osteoarthritis treatment.

BACKGROUND

Typically, orthopedic devices include a frame that comprises at least one support member. When there are multiple support members, the device may include rotational hinges that assist and control movement of the limb. Suitable straps may maintain the brace on the limb, and other features such as pads may relieve pressure of the brace on the limb and surrounding areas.

A predominant orthopedic device is a knee brace. Knee braces are used to stabilize the knee by preventing excessive movement of the knee, or to facilitate movement of the knee. Many braces comprise a frame and have hinges on at least one of the lateral and medial sides of the knee joint. Straps are used to secure the brace to the leg or knee. An injured knee can be fit with an "off the shelf" brace or a "custom-fit" brace, with the selection of the brace depending on the size and shape of an individual's leg.

Many knee braces reduce knee instability following an injury, fatigue or to treat impairment of the knee, particularly if the knee has damaged ligaments. Braces may be recommended for walking, skiing, running, twisting, pivoting, or jumping activities. Besides providing increased stability to the knee, braces may also decrease the risk of injuring the knee or leg, or provide corrective assistance to the knee.

To maximize its supportive, protective and comfort aspects, it is desirable that a knee brace securely and precisely fit the leg of the wearer. While custom-fit braces are made to closely conform to the exact geometry of a leg of a wearer, it is common for the geometry of the leg to change over time requiring even a custom-fit to accommodate a variety of geometries of the leg. As for off-the-shelf braces, these braces must be configurable to accommodate a variety of leg geometries irrespective of the particular geometry of a leg.

In recognizing the need for effective knee braces, various knee braces have been introduced to the marketplace. Such knee braces, however, have comprised relatively heavy, bulky apparatuses that fail to provide ventilation and evenly distribute pressure from the brace on the leg of the wearer. Many contemporary braces are deficient because the braces do not consistently provide or lack adjustment features for forming a firm, comfortable and secure interface between the leg and knee of the wearer and the brace. Because of these drawbacks, many knee braces detract from the user's endeavor.

The features of the embodiments described are provided in recognition of the need for orthopedic braces and components for use therewith that are adjustable in both custom-fit and off-the-shelf braces to achieve superior functional performance characteristics while being comfortable to the wearer when worn. This recognition is realized with the embodiments described.

Knee braces are widely used to treat a variety of knee infirmities. Such braces may be configured to impart forces or leverage on the limbs surrounding the knee joint to relieve compressive forces within a portion of the knee joint, or to reduce the load on that portion of the knee. If knee ligaments are weak and infirm, a knee brace may stabilize, protect, support, unload, and/or rehabilitate the knee.

The knee is acknowledged as one of the weakest joints in the body, and serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any physical activity requiring using the legs.

A healthy knee has an even distribution of pressure in both the medial and lateral compartments of the knee. It is normal for a person with a healthy knee to place a varus moment on the knee when standing so the pressure between the medial and lateral compartments is uneven but still natural.

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or due to aging of the knee.

A major problem resulting from osteoarthritis of the knee is that the smooth cartilage lining the inside of the knee wears away. This leads to a narrowing of the joint space with developing cysts and erosions in the bone ends. Because of the narrowing of the joint, bone comes directly in contact with bone, and an uneven distribution of pressure develops across the knee which may cause the formation of bone spurs around the joint; all ultimately lead to increasing pain and stiffness of the joint.

While there are no cures to osteoarthritis, there are many treatments. Individuals who have a diagnosis of isolated medial or lateral compartmental osteoarthritis of the knee are confronted with a variety of treatment options such as medications, surgery, and nonsurgical interventions. Nonsurgical interventions include using canes, lateral shoe wedges, and knee bracing.

Knee bracing is useful to provide compartmental pain relief by reducing the load on the affected compartment through applying an opposing external valgus or varus moment about the knee joint. Unloading knee braces have been shown to significantly reduce osteoarthritis knee pain while improving knee function.

While known knee braces succeed at reducing pain or at stabilizing a knee joint, many users find these braces to be bulky, difficult to don, complicated to configure, and uncomfortable to wear. Embodiments of the disclosure have streamlined features capable of providing relief for medial or lateral compartmental osteoarthritis, or functional stability of the knee while providing a configuration that has a low profile and unexpectedly provides a more conforming and supportive fit for the orthopedic device.

SUMMARY

Various embodiments described are directed to a versatile orthopedic device arranged to convert between ligament and osteoarthritis treatment, and to accommodate a variety of leg anatomies. According to the embodiments, the orthopedic device is configured as a double-upright brace indicating struts, frame component sections and associated hinges preferably intended to be along both medial and lateral sides of a wearer's leg.

The embodiments are arranged to be cold-formed by a clinician to conform to the individual anatomy of the wearer. Frame components are formed from a metal, such as an aluminum alloy, that will permit "cold-forming" while maintaining sufficient integrity to withstand forces exerted by the wearer. Cold-forming implies that the frame components do not require heating for reshaping, but rather can be bent by suitable means to cater to individual anatomies while retaining sufficient structural integrity while being worn by a user without yielding to various forces exerted by the wearer.

Different frame components and other elements may be formed from materials exhibiting different strengths and other properties enabling the clinician to custom form the device according to specific needs of a wearer. Either or both medial and lateral sides may be reinforced with struts having strength greater than a frame component to increase medial-lateral stability.

The ability to cold-form the frame allows the device to be sold as an off-the-shelf product without the need for fabricating each individual device for an individual anatomy. The device is versatile in the manner of accommodating a variety of anatomies and indications, and may be custom-made as well.

Embodiments may include slots formed on struts that allow a clinician to resize the length of the device to permit short, standard or long versions of the device, and potentially reduce hinge binding on osteoarthritis patients.

In addition to resizing and modifying the shape of the frame components, the device includes means for additionally accommodating anatomy of the leg. The device may include a tibia pad adapted to conform to part of the shape of the second frame component and be adjustable in location along the second frame component to correspond to the tibia of an individual wearer of the brace. As the medial side of the anterior aspect has a generally flat profile corresponding to the tibia and periosteum, and the lateral side has a rounded profile corresponding to the lateral muscle compartment, the second frame component can be contoured due to its malleability to the lower leg. It may be difficult to obtain an accurate match for an individual user along the second component, and the tibia pad can fill the void of the medial side of the second component between the leg and orthopedic device without requiring guesswork of shaping the second frame component itself.

The embodiments preferably have a streamlined and short profile to allow a wearer freedom of movement and reduce weight of the device. The embodiments may enable a short brace ranging from a distance from an outer peripheral edge of the first frame component to an outer peripheral edge of the second frame component when the orthopedic device is in full extension and is about or less than 45 cm. A combined thickness of the first extension and the first strut defining an upright is about or less than 10 millimeters. A thickness of the first frame component extending about a leg may be about or less than 5 millimeters.

A strap kit and method for installing the orthopedic device includes an osteoarthritis strap kit arranged for securing to a basic frame of the orthopedic device by a subshell system. The subshell system, which may be configured as more flexible than the basic frame, is adapted to evenly distribute pressure about a user's anatomy.

The orthopedic device is preferably modular in design to treat a variety of indications, including ACL (anterior-collateral ligament), MCL (medial-collateral ligament), LCL (lateral-collateral ligament) and posterior-collateral ligament (PCL), rotary and combined instabilities; mild to severe ligament laxity, sprain or deficiency; protection and stabilization of ligaments after surgical repair or reconstruction; medial or lateral compartment unloading for unicompartmental osteoarthritis or articular cartilage healing; post-operative rehabilitation and functional support plus unloading protocols requiring medial or lateral joint loads during recovery; functional support with or without varus/valgus alignment; and contact and impact activities.

BRIEF DESCRIPTION OF THE DRAWINGS

The orthopedic device is described regarding the accompanying drawings which show preferred embodiments according to the device described. The device as disclosed in the accompanying drawings is illustrated for example only. The elements and combinations of elements described below and illustrated in the drawings can be arranged and organized differently to result in embodiments still within the spirit and scope of the device described.

FIG. 2A is a front elevational view of a first frame component in an upper frame assembly of FIG. 1 in a non-contoured configuration.

FIG. 2B is a front elevational view of a strut for the upper frame.

FIG. 3A is a perspective view of a first frame assembly in the embodiment of FIG. 1.

FIGS. 8C-8F are perspective views showing modification of the orthopedic device of FIG. 1 with an osteoarthritis strap kit.

FIG. 9 is a schematic view showing a cross-section of a lower leg.

FIG. 10 is a schematic frontal view of adjustment of the tibia pad of FIG. 9 relative to the second frame component of FIG. 4A.

FIG. 11 is a schematic top view showing the tibia pad relative to the second frame component and a liner.

DETAILED DESCRIPTION OF THE VARIOUS EMBODIMENTS

A. Overview

Figure 1:
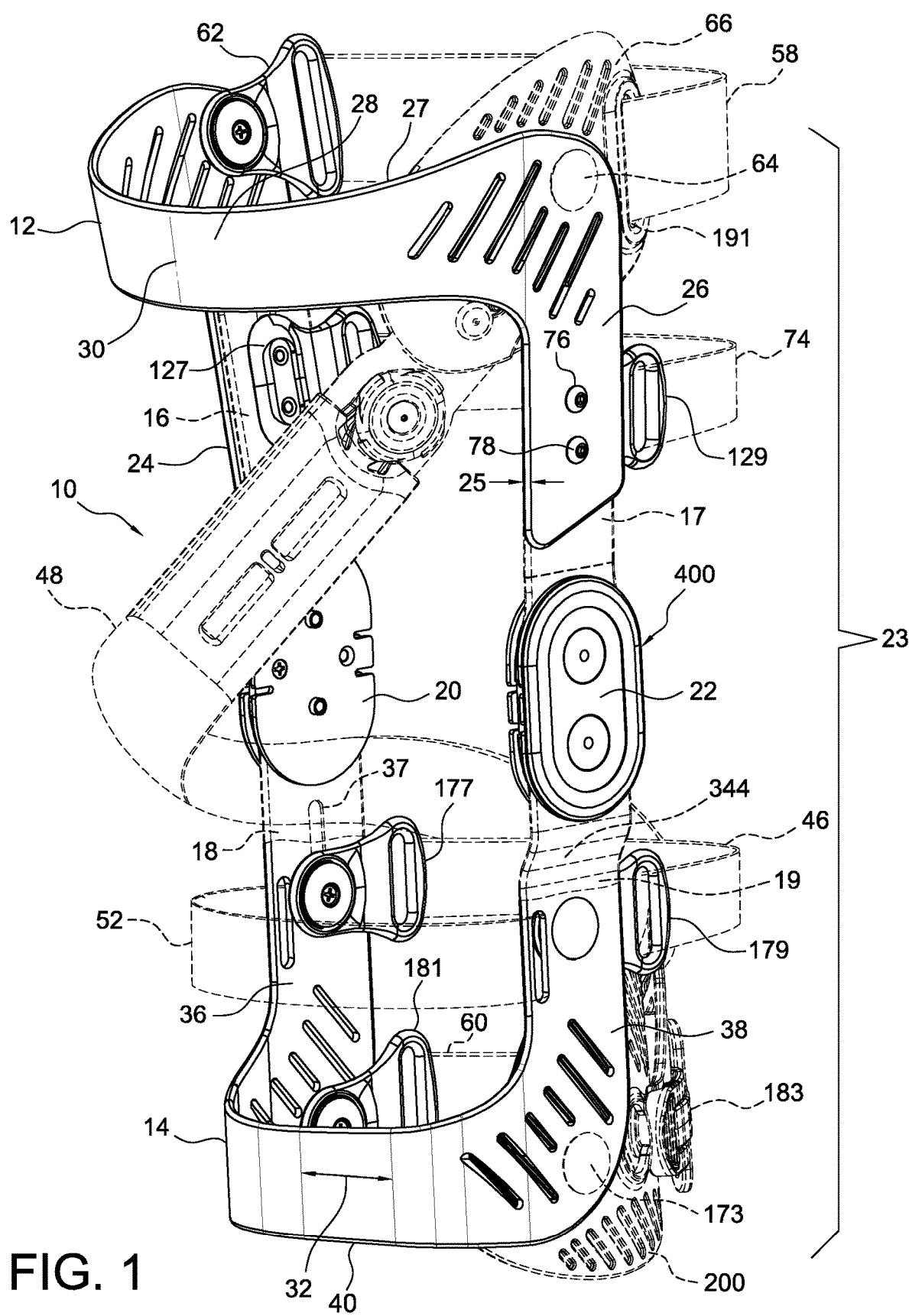
FIG. 1 is a perspective view of an embodiment of an orthopedic device.

A better understanding of different embodiments of the disclosure may be had from the following description read with the accompanying drawings in which like reference characters refer to like elements.

While the disclosure is susceptible to various modifications and alternative constructions, certain illustrative embodiments are shown in the drawings and are described below. It should be understood, however, there is no intention to limit the disclosure to the embodiments disclosed, but on the contrary, the intention is to cover all modifications, alternative constructions, combinations, and equivalents falling within the spirit and scope of the disclosure.

It will be understood that, unless a term is defined in this disclosure to possess a described meaning, there is no intent to limit the meaning of such term, either expressly or indirectly, beyond its plain or ordinary meaning.

Any element in a claim that does not explicitly state "means for" performing a specified function, or "step for" performing a function, is not to be interpreted as a "means" or "step" clause as specified in 35 U.S.C. section 112.

B. Definitions

For ease of understanding the disclosed embodiments of an orthopedic device, the anterior and posterior portions of the orthopedic device are described independently. The anterior and posterior portions of the orthopedic device function together to support and stabilize anatomical portions of the wearer of the device.

For further ease of understanding the embodiments of an orthopedic device as disclosed, a description of a few terms is necessary. As used, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. The term "anterior" has its ordinary meaning and refers to a location ahead of or to the front of another location.

The terms "rigid," "flexible," "compliant," and "resilient" may distinguish characteristics of portions of certain features of the orthopedic device. The term "rigid" should denote that an element of the device is devoid of flexibility. Within the context of frame or support members or shells that are "rigid," it should indicate that they do not lose their overall shape when force is applied, and they may break if bent with sufficient force. The term "flexible" should denote that features are capable of repeated bending such that the features may be bent into retained shapes or the features retain no general shape, but continuously deform when force is applied.

The term "compliant" is used to qualify such flexible features as conforming to the shape of another object when placed in contact therewith, via any suitable natural or applied forces, such as gravitational forces, or forces applied by external mechanisms strap mechanisms. The term "resilient" is used to qualify such flexible features as returning to an initial general shape without permanent deformation. As for the term "semi-rigid," this term is used to connote properties of support members or shells that provide support and are free-standing; however, such support members or shells may have some degree of flexibility or resiliency.

C. Various Embodiments of the Orthopedic Device and Components for Use Therewith According to an embodiment of the disclosure illustrated in FIG. 1, a versatile orthopedic device 10 includes a basic frame including a first frame component 12 defining first and second extensions 24, 26 and a center section 28 spanning between the first and second extensions 24, 26 and having a center line 30; a second frame component 14 defining first and second extensions 36, 38 and a center section 40 spanning between the first and second extensions 36, 38; and a hinge assembly 400 including first and second hinges or joints 20, 22 connecting the first and second frame components 12, 14 by first and second struts.

The second frame component 14 may define a flattened region 32 preferably located between the center section 40 and one of the first or second extensions 36, 38. The opposing side preferably does not include such flattened region. This flattened region is a solution for solving the problem of the anatomy of the medial side of the lower leg in relation to the discussion on FIG. 9, and as discussed in connection with another solution discussed in connection with FIGS. 10-13. Rather than including an insert, as in FIGS. 10-13, the lower frame component 14 is permanently deformed to the medial side of the lower leg.

The hinges may be selected from a variety of hinges found in orthopedic devices. An exemplary hinge is described in U.S. Pat. App. Pub. 2012/0059296, published Mar. 8, 2012, or U.S. Pat. No. 7,597,675, granted Oct. 6, 2009, and incorporated in its entirety by reference.

The basic frame forms a "double upright" brace or "cage-style" device adapted as a knee brace. While the exemplary embodiment shows the first frame component in a proximal location along an anterior side and a second frame component in a distal location also along an anterior side, the basic frame is not limited to this configuration. The first frame component can be arranged along an anterior side, while the second frame component can be arranged along a posterior side to form a "step through design." Both the first and second frame components may be arranged along the posterior side.

Suitable padding may be provided along the frame portions of the orthopedic device. The padding may be constructed in a variety of types, and a preferable padding is edge bound and thermoformed. The padding preferably extends beyond the periphery of the frame components to minimize discomfort and assure the wearer's anatomy is sufficiently protected. An exemplary padding may be found in U.S. Pat. No. 8,585,623, granted Nov. 19, 2013 or U.S. Prov. App. No. 62/103,678, filed Jan. 15, 2015, incorporated herein by reference.

In a variation, the orthopedic device 10 has first and second struts 16, 17 securing to and overlapping the first and second extensions 24, 26 of the first frame component 12 and securing to the first and second hinges 20, 22. In a variation, the orthopedic device 10 also includes first and second struts 18, 19 securing to and overlapping the first and second extensions 36, 38 of the second frame component 14.

The overlap 25 may be the entirely or substantially along the length of the extension of the first and second frame components. As it is desired to maintain a streamlined configuration, a combined thickness of the extensions and the first struts may be about or less than 10 millimeters.

Various removable fasteners 76, 78, such as Chicago screws, are used to secure the struts to the frame components. Any of the struts 16, 17, 18, 19 may include an adjustment system, such as slots (as shown as 37 in FIG. 1 or in FIG. 5A) to enable lengthening or shortening the orthopedic device along length 23. A distance 23 from an outer peripheral edge 27 of the first frame component 12 to an outer peripheral edge 29 of the second frame component 14 when the orthopedic device is in full extension (knee is in 0 degrees of flexion) is about or less than 45 cm.

The adjustment system may, in part, allow for correction of leg curvature by forming a lateral inward or outward angle of the upper frame in relation to the lower frame, as discussed in U.S. Pat. No. 6,875,187, granted on Apr. 5, 2005, in relation to the securable slidable engager described, and U.S. Pat. App. Pub. No. 2013/0144197, published Jun. 6, 2013, incorporated herein by reference.

In an exemplary embodiment, the first strut 16 defines an elongate slot at a first end (generally in the proximal direction), and the fasteners 76, 78 extend through openings defined by the first frame component and the slot. When the fasteners are loosened, the first strut is slidable relative to the first frame component and secured to the first frame component without movement by regulation of the first fastener.

The first and second frame components are preferably constructed from aluminum and may be malleable from a cold forming treatment to allow for easy customization of the frame elements to a particular leg shape. Other exemplary materials that may be used for constructing the frame include metals such as titanium, and steel, thermoset resin composite systems including glass or carbon fibers, and thermoplastics rendered rigid by way of material composition and geometry of the frame members. The first and second frame components may be formed from different materials or materials having different properties such as strength and rigidity and are not limited to be formed from the same materials.

The struts are preferably constructed from a malleable material such as an aluminum alloy. The struts may be constructed from an aluminum alloy stronger than an aluminum alloy forming the first frame component. The frame components may be constructed from aluminum alloys 5052 or 6061, and the struts may be formed from the same alloys or stronger alloys. The clinician can select which types of struts to use on the basis of the needs of a wearer such that the orthopedic device may be furnished as a strap kit with a selection of different struts available for the clinician to use. The struts are not limited to being selected from the same material but each strut or pairs of struts may have a material different from another depending on the indications of an individual wearer.

Even if the frame components and the struts are formed from the same or substantially same materials, the struts may be extended along an inner surface of the extensions and reinforce the frame components. This arrangement provides flexibility in tailoring the rigidity of the lateral and medial sides of the orthopedic device, and eliminates permanently fixing the rigidity of sides of the orthopedic device in that the struts may be removed and switched as desired.

Suitable straps 46, 58, 60, 74 may depend from the first and second frame components 12, 14. D-rings or suitable means 62 may be pivotally secured by fasteners 64 to the frame components. A tibial strap 46 may extend between the first and second extensions 36, 38, and include a cover or sleeve to cover any strap ends or other items forming part of or protruding from the strap 46 to provide a streamlined appearance.

In the embodiment of FIG. 1, an osteoarthritis strap kit 48 secures to the basic frame. In a variation shown in FIG. 2A, the strap 48 includes a hook element 54 securable to a keyhole 56 formed along the center section 28 at a first side of the first frame component 12 and spirals the first side of second frame component 14 while crossing over to the second side generally proximate the second hinge 22.

A flexible subshell 66 may secure to first frame component 12. The flexible subshell is secured to the first frame component 12, and has a first end extending laterally beyond the first side portion to flex relative to a side portion of the first frame component. The subshell may have a contoured edge extending beyond the peripheral contour to flex relative to the frame peripheral contour. The subshell may be mounted along an interior surface of the first frame component. The strap 58 may secure to or over the subshell 66 to evenly distribute pressure over the wearer's anatomy.

The subshell 66 may selectively attach to the first frame component 12 and has protrusions extending through slots formed by the first frame component 12 to prevent pivoting of the subshell 66 relative to the first frame component. The fastener 64 for the D-ring 62 may extend through the subshell 66 to prevent it from slipping away from the first frame component. Subshells may be attached at any portion of the first and second frame components and the method described above is merely exemplary.

The osteoarthritis strap kit transforms the orthopedic device into an unloading type knee brace, under the principles described in U.S. Pat. No. 7,198,610, granted Apr. 3, 2007, and U.S. Pat. No. 5,277,698 granted Jan. 11, 1994, both incorporated in their entirety by reference. The strap may be a strap tightener assembly for a strap assembly for an orthopedic device discussed in U.S. Pat. App. Pub. No. 2013/0184628, published Jul. 18, 2013, and incorporated in its entirety by reference.

FIGS. 2A-4B depict alternative embodiments of the first and second frame components 111, 114, respectively, in a flat condition prior to contouring, unlike in FIG. 1, and hence are in a non-contoured configuration, or in a contoured configuration, as noted. The first and second frame components 111, 114 are arranged similarly as the components in FIG. 1. It will be noted in the following examples that the first frame component 111 embraces both the first or upper frame, and the struts for each side of the first frame. For simplicity, a single strut is described by such strut may be oriented or adapted for both sides of the first frame 112.

Referring to FIG. 2A, the first or upper frame 112 of the first frame component 111 defines first and second extensions 124, 126 and a center section 128 spanning between the first and second extensions 124, 126 and having a center line 130. The center line 130 defines a location of the center section 128 having a shorter height 142 than areas outside of the center line 130. The shorter height 142 facilitates bending of the center portion 128 by a clinician to customize the contour of the center section 128 to an individual wearer.

The center section 128 forms a dip or slight gradual swoop 152 toward the center line 130 from corners 132, 134 defined at the junction of first and second sides of the center section 128 and the first and second extensions 124, 126, respectively. The dip 152 provides contouring to the anatomy of the wearer and enables a pleasing aesthetic appearance.

The first and second extensions 124, 126, which are along the longitudinal length of a leg, are oriented at an angle less than 90 degrees in the pre-contouring condition to better approximate the anatomy of the wearer. As the orthopedic device is streamlined and minimal in size, the length of the first and second extensions 124, 126 are preferably short, as denoted by length 154. The length 154 (taken from inner corners 150) of the extensions 124, 126 may be shorter than a length 153 of the center section 128 from the inner corners 150 to the center line 130. If desired to lengthen the orthopedic device, regulation of the position of the struts (as discussed in relation to FIG. 1) may be had by adjusting the slot of the struts relative to positioning holes 144 on the extensions 124, 126 for receiving fasteners.

The first frame 112 defines first and second wing sections 132, 134 opposite the corners 150 and extending in an opposite direction to the center section 128. The wing sections 132, 134 provide extra material and area to the first frame 112 to accommodate various attachments such as D-rings for supporting straps and subshells. The wing sections 132, 134 extend from the inner corners 150 to outer corners 146, and have apertures 148 for securing D-rings, slots 170 for easing bending for contouring the first frame component 111, ventilating the frame component, and coupling to a subshell.

Figure 5A:
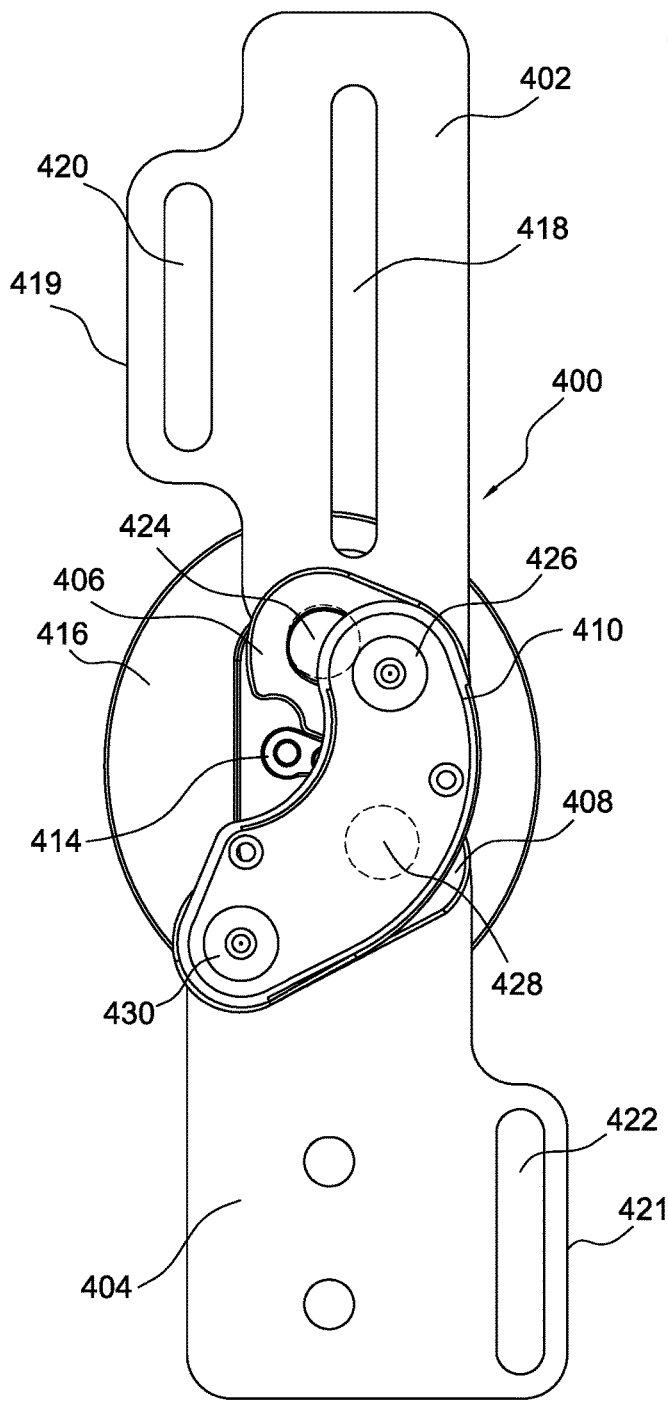
FIG. 5A is a side elevational view of a hinge assembly embodiment.
Figure 5B:
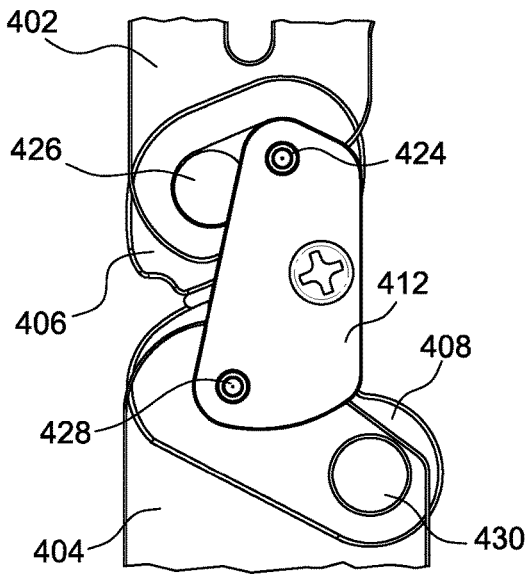
FIG. 5B is a rear schematic portion view of the hinge assembly of FIG. 5A.
Figure 5C:
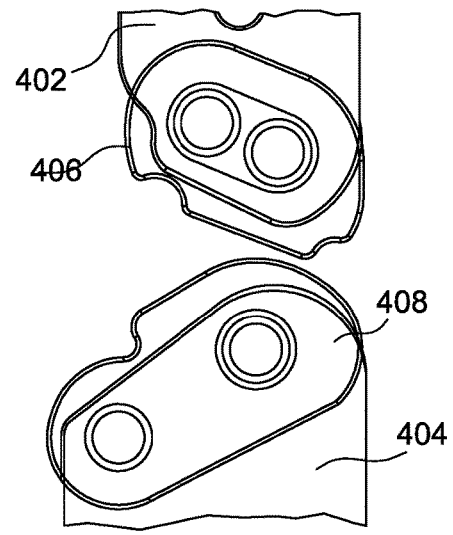
FIG. 5C is a front schematic portion view of the hinge assembly of FIG. 5A without various hinge components.
Figure 5D:
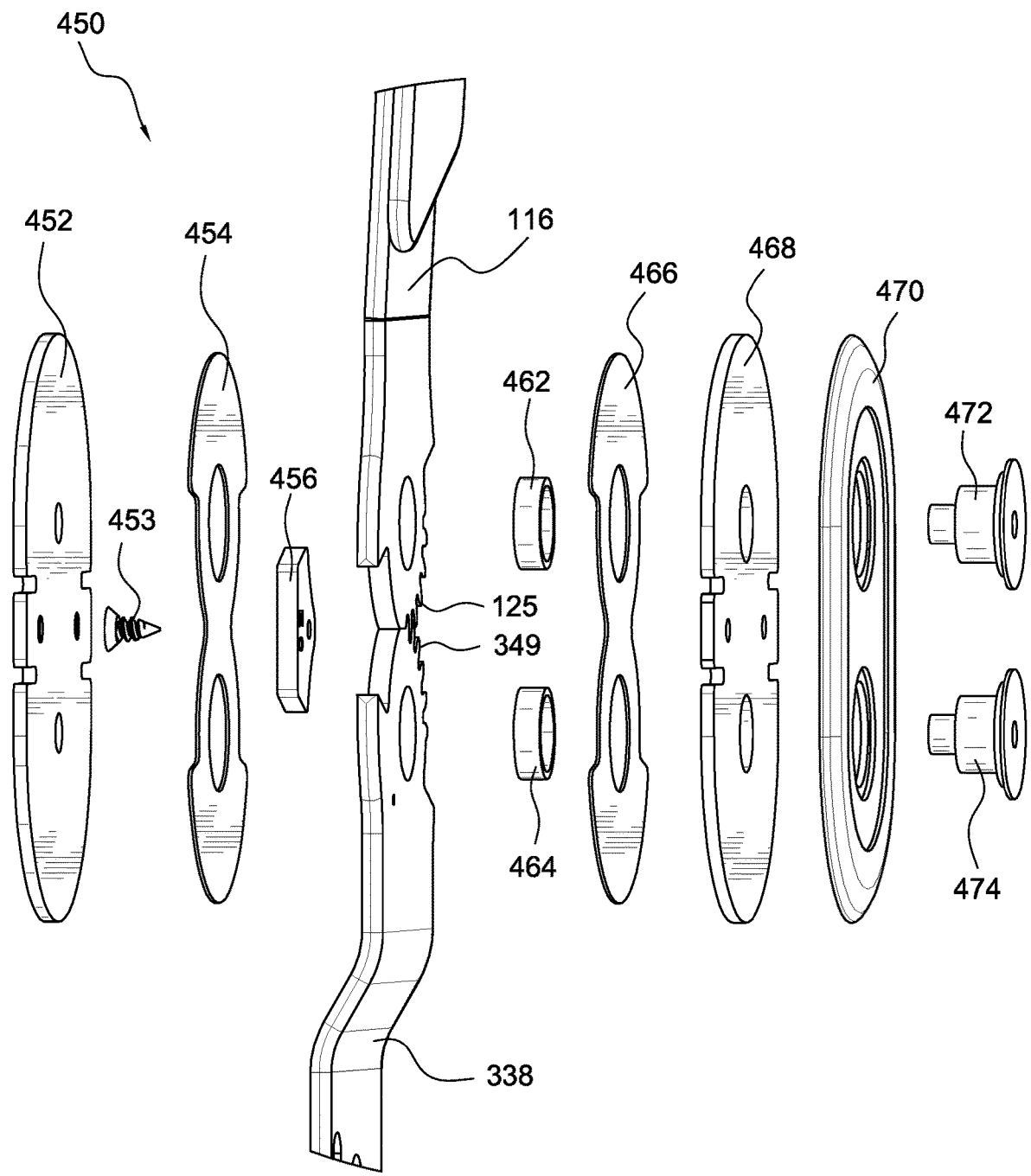
FIG. 5D is a perspective schematic view of a hinge assembly in FIG. 1 and including the first frame assembly of FIG. 2A and the second frame component of FIG. 4B.

Turning to FIG. 2B, the strut 116 (which may comprise the shape of either strut 16 or strut 17 in the embodiment of FIG. 1) includes a first end 121 contoured to fall within the width of the first and second extensions 124, 126, and a second end 123 having a gear profile 125 for forming part of a hinge, as shown in FIG. 5D. The second end 123 also defines an extension stop 119 for limiting extending of the hinge, and an opening 122 for forming part of the hinge, as discussed in more detail in relation to FIG. 5D.

Figure 3B:
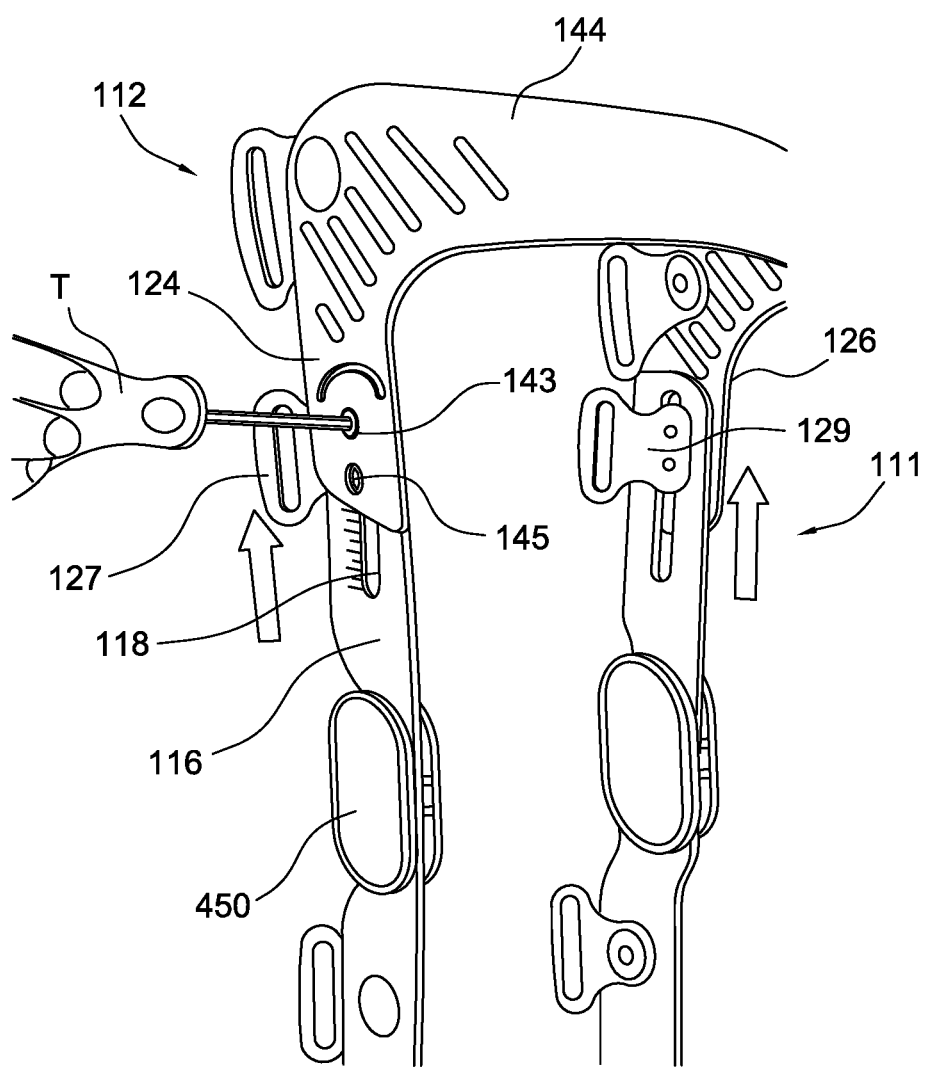
FIG. 3B is a schematic view of adjustment of the first frame assembly in the embodiment of FIG. 1.

An elongate slot 118 extends downwardly from the first end 121 toward the second end 123. The elongate slot 118 is adapted to receive fasteners, as shown in FIGS. 3A and 3B, and permit sliding movement of the strut 116 relative to the extensions and affixation thereof at a desired location along the extensions. Indicia 120 are provided along the length of the slot 118 to enable a clinician understanding of relative lengths of both struts, as in the embodiment of FIG. 1.

Referring to FIG. 3A, a coupling part 129 is located on a first or inner side of the strut 116, and the extensions of the first frame 112, such that the strut 116 located between the coupling part 129 and a corresponding one of the extensions. The coupling part 129 defines a D-ring portion 131 having a slot 133 for receiving a strap. The D-ring portion 131 extends toward and/or beyond the periphery of the first frame component 112 and flexibly therefrom for receiving a strap. Both lateral and medial, or first and second sides of the first frame component 112 include coupling parts 129, and a strap extends therebetween.

While a D-ring may be formed from the strut 116 material itself and be integrated therewith, the coupling part 129 is advantageous in that it can be adjusted in height according to the location of the strut relative to the extensions. This enables a floating adjustment of the D-ring and corresponding strap according to the height of the first frame component as a whole.

The coupling part 129 defines a head portion 137 that has a width less than a width of the strut but greater than the slot 118. The head portion 137 defines a recessed portion 139 that may have an elongate configuration oriented generally parallel to the slot 118. The recessed portion 139 further defines at least one aperture 141 for receiving at least one fastener 143, 145 that is arranged to extend through the coupling part 129, slot 118 and the extension. The recessed portion 139 is arranged to minimize projection of the at least one fastener 143, 145 into or against the user of the orthopedic device. One end of the at least one fastener is retained or abuts the coupling part 129 within the recessed portion 139 and another end of the at least one fastener engages an outer side of the extension.

The coupling part 129 is preferably formed from a single and continuously monolithic piece to maintain stabilization as both support with the head portion 137 for the at least one fastener and height adjustment of the first frame component 111, and for maintaining the strap between opposed sides (i.e., medial and lateral) of the first frame component even when the height of the first frame component is adjusted in height. A hinge or thinned portion 135 from the material forming the coupling part is located between the D-ring portion 132 and the head portion 137 for permitting some laxity or adjustability of the coupling part when tensioning a strap carried by coupling parts. The D-ring and the head portions 133, 137 may be substantially rigid, particularly the head portion 137 for securely receiving the at least one fastener, whereas the hinge portion 135 is flexible at least in part due to its thinned profile.

FIG. 3B shows that the at least one fastener 143, 145 is loosened by a tool T from the outer side of the extension for height adjustment of the first frame component 111. The at least one fastener is preferably retained between the coupling part 129, the struts 116 and the extensions 124, 126. A clinician can adjust the height when the at least one fastener 143, 145 is loosened, and tighten at a desired setting by referring to the indicia on the strut.

Figure 4A:
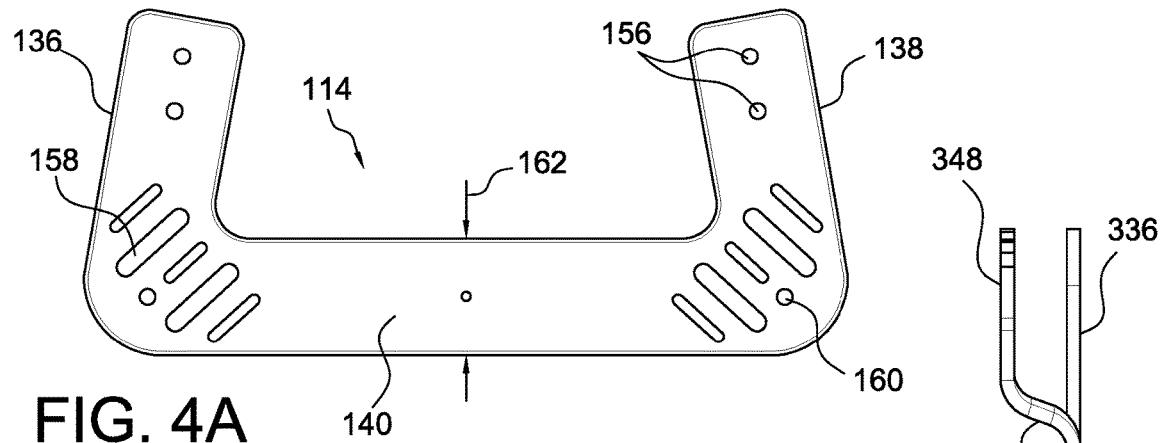
FIG. 4A is a front elevational view of a second frame component for an embodiment of the orthopedic device in a non-contoured configuration.

As illustrated in FIG. 4A, an embodiment of the second frame component 114 defines first and second extensions 136, 138 and a center section 140 spanning between the first and second extensions 136, 138. The second frame component 114 may have positioning holes 156 for receiving fasteners securing to struts (not shown), slots 158 for securing to subshells, and apertures 160 for securing D-rings. The second frame component 114 may be configured to include struts, as in FIG. 2B, adjusting the height of the second frame component, and may be similarly arranged as with the struts for the upper frame component.

Alternatively, the center section 128 may have a uniform height, as shown in the second component 114 by way of uniform height 162 along the center section 140. The center section 140 of the second frame component 114, however, may likewise have similar features as the center section 128 of the first frame component such as the variable height and dip.

Figure 4C:
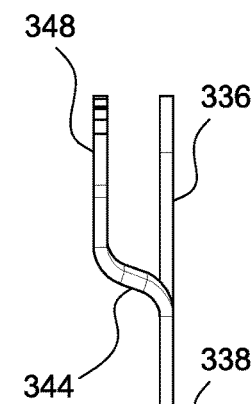
FIG. 4C is a side elevational view of the second frame component in FIG. 4C.
Figure 4B:
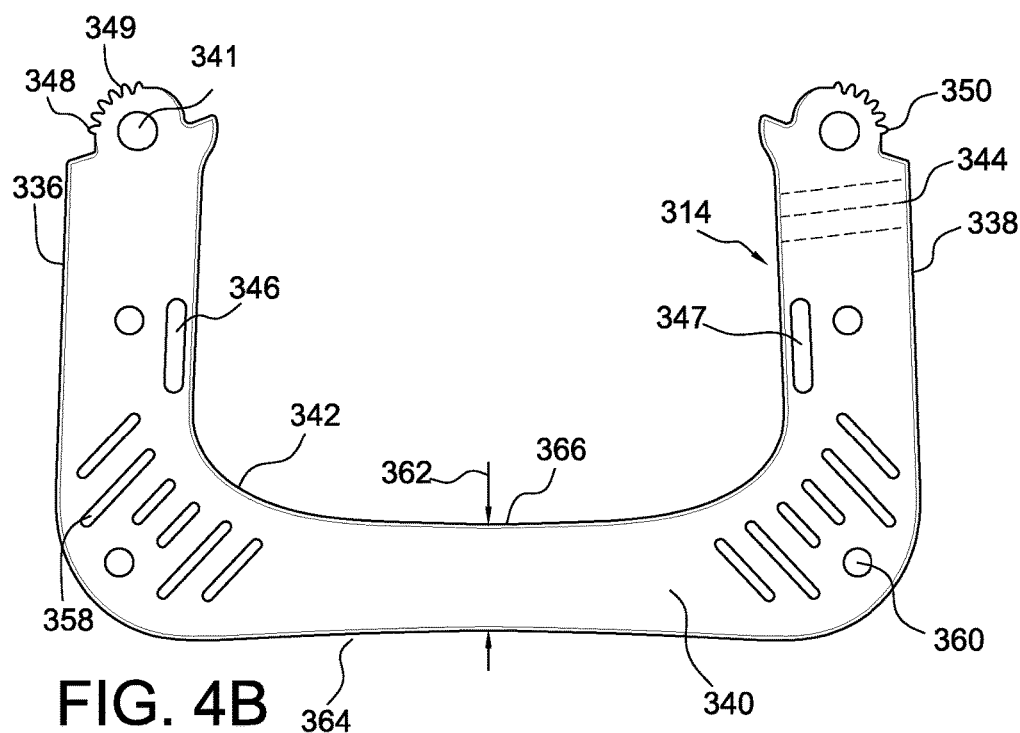
FIG. 4B is a front elevational view of a variation of the second frame component in FIG. 4A in a non-contoured configuration.

FIG. 4B shows a variation of the second component 314. The second component 314 includes first and second extensions 336, 338 and a center section 340 spanning therebetween. Unlike in the embodiment of FIG. 4A, the first and second extensions 336, 338 are substantially upright, generally forming a right angle relative to the center section, and do not exhibit the angled or acute angle arrangement of FIG. 4A.

A fillet 342 exists between each of the first extension 336 and the center section 340, and the second extension 338 and the center section 340, to provide a wider transition between the sections. As in the first component, the center section 340 tapers in height 364 toward a center point 366 of the center section 340 relative to the extension of the first and second extensions 336, 338. In addition, the width 362 of the center section 340 tapers toward the center point 366 to reduce the weight of the center section and minimize extension of the center section along the leg, as it is desirable the orthopedic possesses a streamlined footprint over the leg of a wearer. The first component may likewise have its center portion adapted similarly to the second component of FIG. 4B.

To minimize the features added to the frame component, either of the frame components can have slots for receiving various straps. In the example of FIG. 4B, the second frame component 314 has slots 346, 347 adapted for receiving a tibia strap, as shown in FIG. 1. The second component 314 defines slots 358 for securing to subshells, and apertures 360 for securing D-rings.

FIGS. 4B and 4C depict the second frame component 314 as having an indent 344, preferably formed on the medial side of the orthopedic device. The indent 344 is adapted for conforming to the anatomy of the leg on the medial side as this configuration tracks the natural curvature of a medial leg.

The second frame component 314 may include end portions 348 at the first and second extensions 336, 338, that are adapted to directly engage the hinge assembly and forms part of the hinge in a polycentric hinge arrangement as evidenced by the gear profile. The end portions 348 may include apertures 341 through which a pin of a hinge engage. The end portions 348 can be modified to receive hinge covers 406, 408, as used in the hinge assembly 400 of FIG. 5C, such that the hinge covers 406, 408 are adapted for engagement.

In the illustrated embodiment, the end portions 348 include a gear profile 349, and an extension stop 350, as in the upper frame 112. Such configuration is preferably used in the hinge variation of FIG. 5D.

FIGS. 5A and 5B illustrate a hinge assembly 400 that may be used in the orthopedic device, and enables securing of the first and second frame components 112, 114 at various locations. The hinge assembly 400 is preferably provided on both sides of the orthopedic device.

The hinge assembly 400 includes first and second struts 402, 404 having first and second end hinge covers 406, 408, respectively. The first and second struts 402, 404 are secured to one another by an outer plate 410 and an inner plate 412, connecting via hinge fasteners or pins 424, 426, 428 and 430. A rotation stop 20, having a variety of geometries depending on the desired rotation, is insertable between the first and second hinge covers 406, 408. A condyle plate 416 may secure to the inner side of the hinge assembly 400, and a suitable pad may be secured to the condyle pad. The hinge components described above may function similarly to the hinge described in U.S. Pat. App. Publ. No. 2012/0059296, published on Mar. 8, 2012, and incorporated by reference.

The struts 402, 404 preferably form protrusions 419, 421 forming strap slots 420, 422. In the depicted embodiment, the protrusions extend from opposing sides of the hinge assembly 400 to receive the posterior upper leg strap 74 in FIG. 2, and the anterior lower leg or tibial strap 46, in FIG. 1. The upper leg strap 74 and the lower leg strap 46 counteract with one another to retain, at least in part, the orthopedic device on the leg of the wearer. The protrusions 419, 421 preferably are arranged to extend sufficiently beyond the first and second frame components so the frame components do not interfere with the straps regardless as to the height position the first and second frame components secure to the hinge assembly, and specifically the first and second struts 402, 404. The protrusions 419, 421 eliminate the need for additional features, such as D-rings, to be assembled to the hinge assembly.

The first strut 402 shows how the hinge assembly 400 may be adjustably secured to the first component. The first strut 402 includes a slot 418 permitting height adjustment of the first component relative to the strut assembly 400 such that the fasteners 76, 78 may be adjustably secured and tightened at a preferred height for an individual user of the orthopedic device. The strut assemblies at both the lateral and medial sides of the orthopedic device may include the slot 418 for uniform, symmetric height adjustment or asymmetric height adjustment depending on the user's leg anatomy and length. The second strut 404 may likewise include a slot similar to the slot 418 for height adjustment of the second frame component relative to the hinge assembly.

In the event the orthopedic device is converted for use as an osteoarthritis brace, the fasteners 76, 78 may be loosened yet still engaging the hinge assembly and the first frame component so that they are slidable and securable against each other, as taught in U.S. Pat. No. 6,875,187. The motion enable and variable angular relationship can be modified to treat inward or outward leg curvature through correction of the knee joint orientation. Alternatively, the fasteners may be secured to maintain an angular mismatch relative to the hinge assembly on an opposite side of the leg.

FIG. 5D illustrates a hinge assembly 450 in combination with the first frame component of FIG. 3A and the lower frame component of FIG. 4B. The hinge assembly 450 is beneficial in that it employs the frame components themselves and reduces parts for orthopedic device as a whole. The gear profiles 125, 349 of the first and second frame components, respectively, engage one another and are biased or enabled for rotation by rivets 472, 474 extending through the openings 122, 341, respectively. The rivets 472, 474 may be received by bearing rings 462, 464 located within the openings 122, 341, and arranged for facilitating rotation of the first and second frame components. Plates 454, 468 may serve as bearings or washers for stabilizing movement of the first and second frame components relative to the hinge assembly and inner and outer covers 452, 470 provide anchoring for the rivets 472, 474. An extension or flexion stop 456 may be securable to the hinge assembly 450 and by being engaged to the plates 454, 468 by a fastener 453. The extension or flexion stops can be arranged as in U.S. Pat. App. Pub. No. 2012/0059296.

Figure 6A:
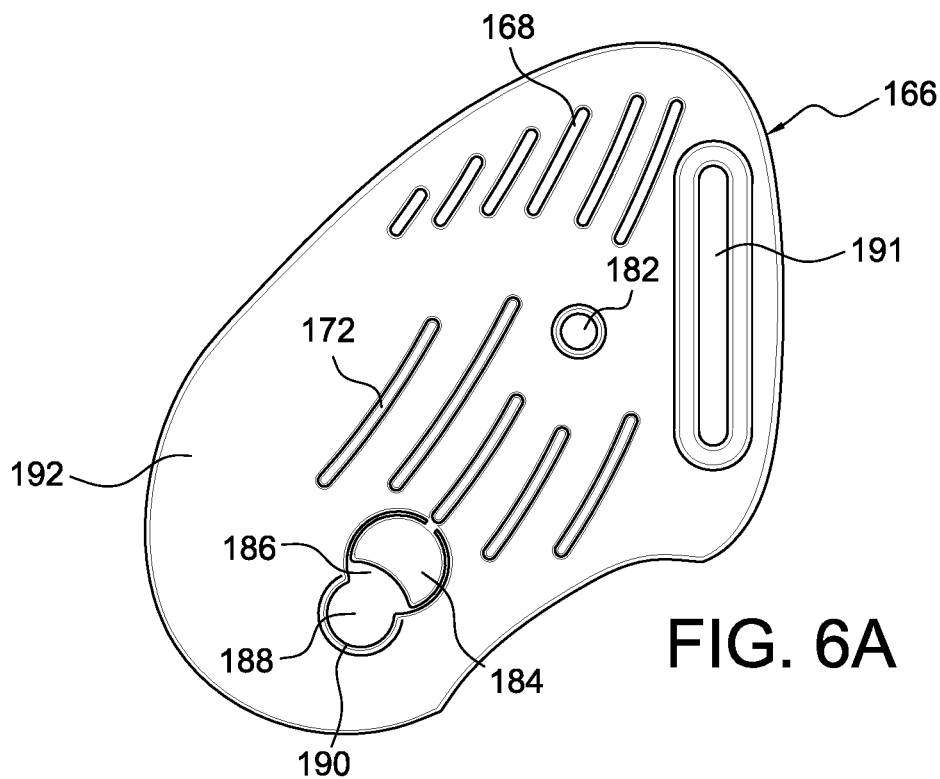
FIG. 6A is a plan view of a first subshell for use with the first frame component of FIG. 2A.

FIG. 6A shows an exemplary embodiment of a subshell 166 that may be attached to the first frame 111 of FIG. 3, and be used to support a first end of a strap tightener assembly to eliminate the need for any key-hole or similar provisions in the frame components. The periphery or profile 192 of the subshell, at least at a rearward side, should extend beyond the corresponding frame component with the strap tightener assembly, particularly for an upper leg.

The subshell defines a plurality of slots 168 at a rear end to facilitate bending of the subshell and ventilate the subshell over the wearer's anatomy as the subshells are preferably intended to spread over a greater area of a wearer's anatomy to evenly distribute pressure. The subshell 166 defines an aperture 182 for receiving a fastener (as discussed regarding FIG. 2) to assure the subshell secures to the frame component. The subshell 166 likewise may define a keyhole 184 having a larger portion 186 for receiving a hook element (as in FIG. 1) of the strap tightener assembly, and a smaller portion 188 for locking the hook element with the subshell 166. A reinforcing edge 190 may be provided about the smaller portion 188 to reinforce the subshell 166 whereat the strap tightener assembly may pull at its greatest.

Figure 6B:
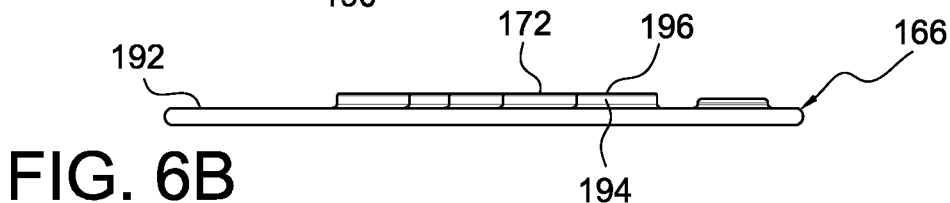
FIG. 6B is an elevational view of the first subshell of FIG. 6A.

Referring to FIG. 6B, the subshell 166 may include locking elements 172 for engaging the through-extending slots 170 defined by a corresponding frame component. The locking elements 172 may include protruding necks 194 with a head portion 196 adapted to snap through and connect to the material of the frame component about the through-extending slot. While shown as being elongate, the locking elements may be formed from a variety of shapes.

Figure 7:
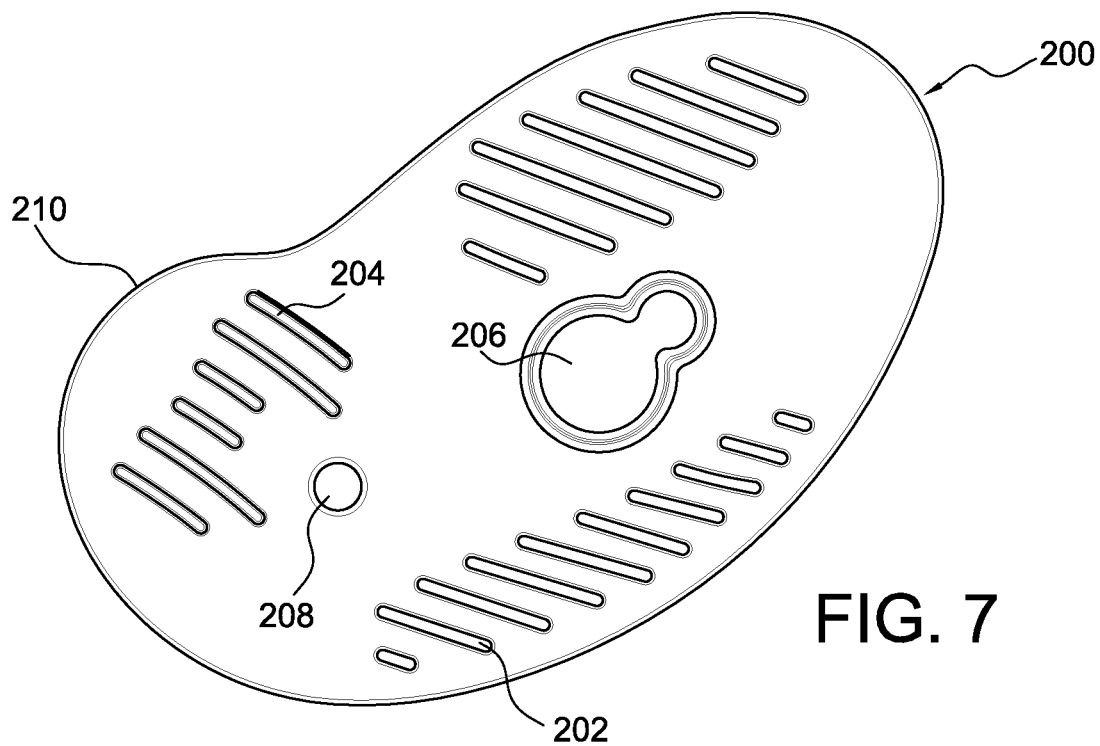
FIG. 7 is a plan view of a second subshell for use with the second frame component of FIG. 4B.

FIG. 7 depicts a second subshell 200 for attachment to the second frame component 114 of FIG. 4, and has a periphery or profile 210 adapted to anatomy of a lower leg. The second subshell 200 includes a key-hole 206 similar to the first subshell, and slots 202, locking elements 204, and an aperture 208.

A method of converting an orthopedic device from a ligament brace to an osteoarthritis brace in any of the aforementioned embodiments may include securing first and second subshells to a first side of the first component and the second component; attaching a first end of a strap to the first subshell, spiraling the strap across a second side of the first component opposite the first component and extending the strap to the second subshell; and attaching a second end of the strap to the second subshell.

Figure 8A:
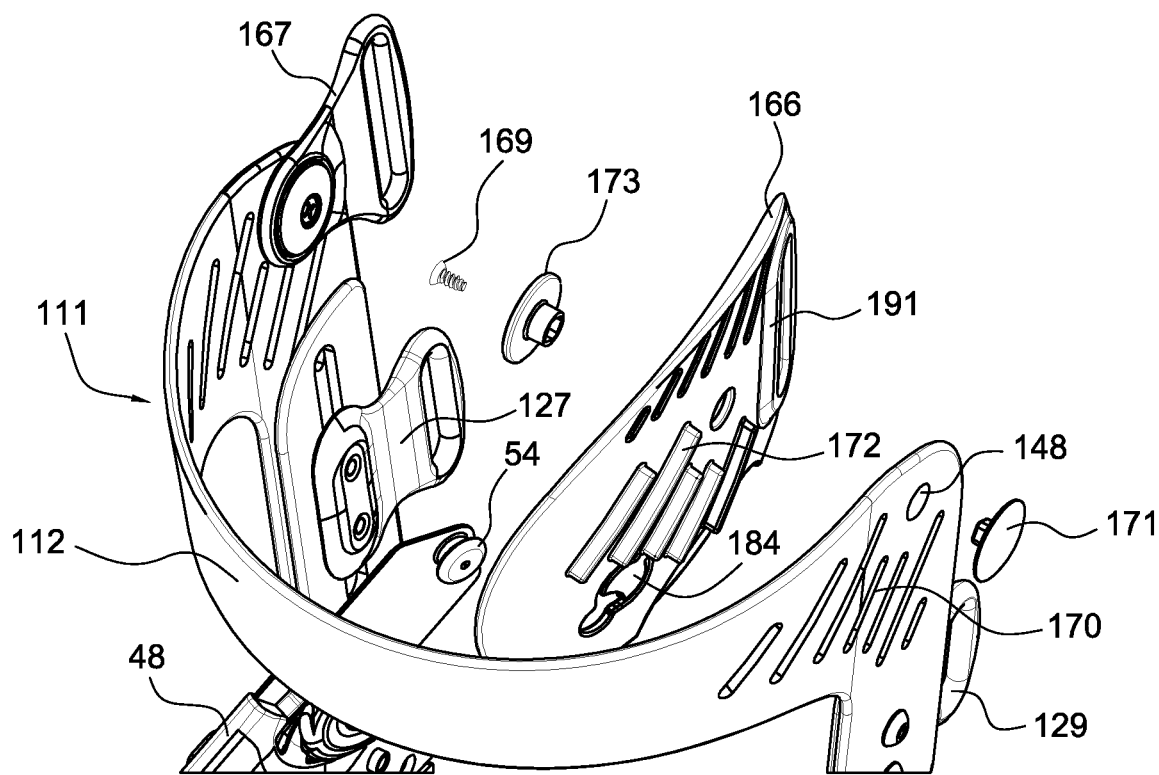
FIG. 8A is a perspective view of modification of the first frame assembly of FIG. 2A with an osteoarthritis strap kit.
Figure 8B:
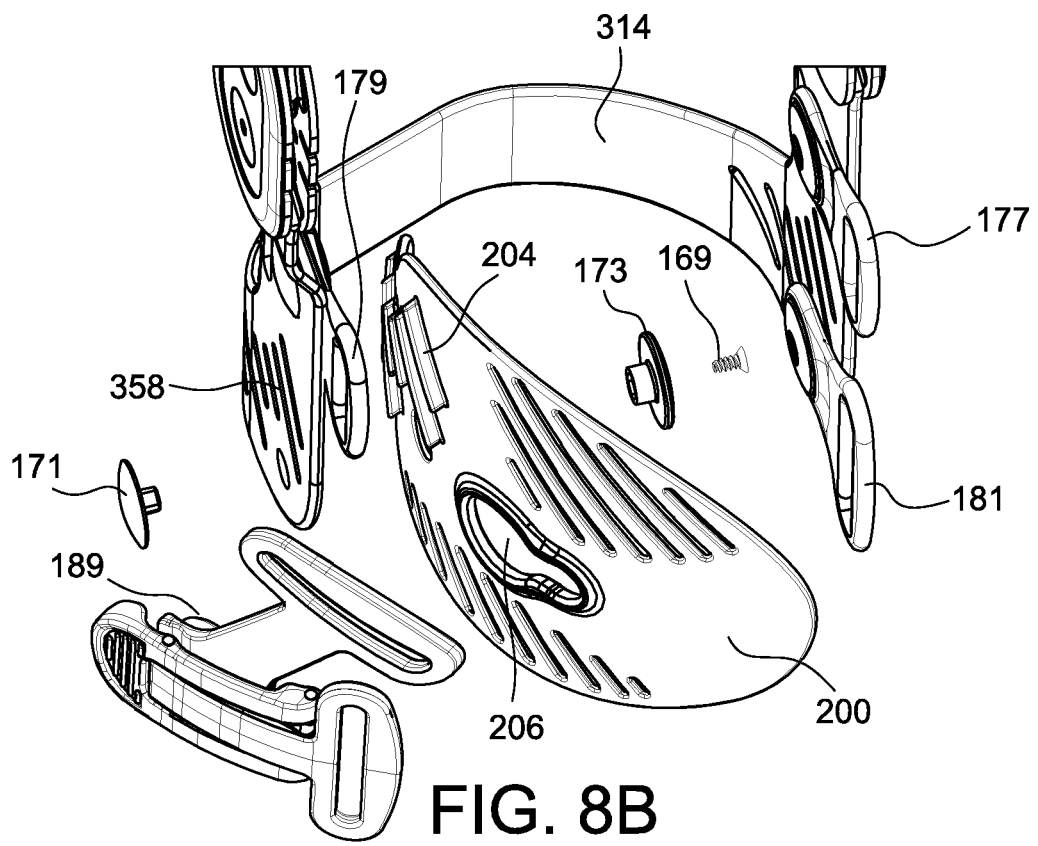
FIG. 8B is a perspective view of modification of the second frame assembly of FIG. 4B with an osteoarthritis strap kit.

FIGS. 8A and 8B exemplify how the first and second subshells 166, 200 couple to the first and second frame components 111, 114 for coupling the osteoarthritis strap kit 48 to the orthopedic device 10 in FIG. 1. The strap kit 48 may have a hook element 54 that engages a keyhole 184 of the first subshell 166.

Referring to FIG. 8A, the locking elements 172 engage the first frame 112 by the through-extending slots 170. A fastener assembly may be arranged for securing the subshell 166 to the first frame 112, as taught in U.S. Pat. App. Pub. 2013/0331751, published on Dec. 12, 2013. The fastener assembly includes a first cap 171 that extends through the aperture 148 to engage a second cap 173 arranged for receiving a post or male portion of the first cap 171 by a female portion of the second cap 173. A fastener 169 secures the first and second caps 171, 173 to one another, and retains the subshell 166 to the first frame 112.

The subshell 166 is mountable to either of first or second sides of the first frame 112. A D-ring assembly 167 may be located on an opposed side of the first frame 112 where the subshell 166 is not located, whereas the subshell 166 includes a slot 191 for receiving a strap which may span between the subshell and the D-ring assembly. The area of the subshell having the slot 191 preferably extends beyond the first frame and the area may have some flexibility to permit better tensioning of the strap against a leg of a user. Coupling parts including D-ring portions 127, 129 may likewise be located below the subshell and or be formed by the aforementioned coupling parts in FIGS. 3A and 3B.

The subshell 200 is similarly arranged as the subshell 166 and with locking elements 204 engaging or being retained by slots 358. A corresponding D-ring assembly 181 may operate with the subshell 200 to support a strap. D-ring assemblies 177, 179 may be located above the subshell for securing a supplementary strap. A buckle assembly 189, as taught in U.S. Pat. No. 7,198,610 may form part of the strap kit 48, and engage a keyhole 206 of the subshell 200.

FIGS. 8C-8F exemplify how the strap kit 48 may be arranged to treat medial or lateral compartmental osteoarthritis in the orthopedic device 10. In FIGS. 8C and 8D, the strap kit 48 is arranged to exert unloading on a first side of the orthopedic device, whereas FIGS. 8E and 8F exert unloading on a second side of the orthopedic device, when the orthopedic device is worn by a user.

Referring to FIGS. 9-12, the orthopedic device may include a tibial pad 230 adapted to accommodate a user's lower leg, and permit universality of the orthopedic device. The tibia pad 230 may fill in a void defined between the second frame component 114 on a side of the brace, such as the medial side for reasons discussed below due to the anatomy of a lower leg.

FIG. 9 shows a cross-section of a lower leg and how the anterior aspect of the lower leg defines an apex. The medial side of the anterior aspect has a generally flat profile corresponding to the tibia and periosteum, whereas the lateral side has a rounded profile corresponding to the lateral muscle compartment. The orthopedic device is generally symmetrical between the lateral and medial sides to allow for universal sizing for left and right legs, and particularly the first and second frame components. Whereas the upper leg or thigh is generally symmetrical among left and right legs, the lower leg is not, as evidenced by FIG. 9. The second frame component can be contoured due to its malleability to the lower leg, and it may be difficult to obtain an accurate match for an individual user. With the tibia pad 230, the shape of the second frame component 114 can be maintained without requiring guesswork of shaping the second frame component 114 itself.

FIG. 10 shows how the tibia pad 230 can be moved to either side of the center section 140 of the second frame component 114, particularly in either corner 141, 143 of the center section 140. The contours of the corners 141, 143 are symmetrical with one another, and the contour of the profile 240 permits adjustment of the tibia pad 230 at a variety of portions at each corner 141, 143 for adjustment to a user's individual anatomy, and for either left or right leg use. As shown in FIG. 10, the tibia pad is preferably sized and configured to fit within the width 162 of the center section 140.

FIG. 11 illustrates the tibia pad 230 against the inner surface 246 of the second frame component 114, and with the profile 240 adapted to the shape of the center section 140. A liner 244 may be placed against the tibia pad 230 and the inner surface 246 of the second frame component 114. The liner 244 is pliable and conforms to the shape of the second frame component 114 and the tibia pad 230. The liner 244 may comprise foam and enables a generally uniform surface against the user's leg.

Figure 12A:
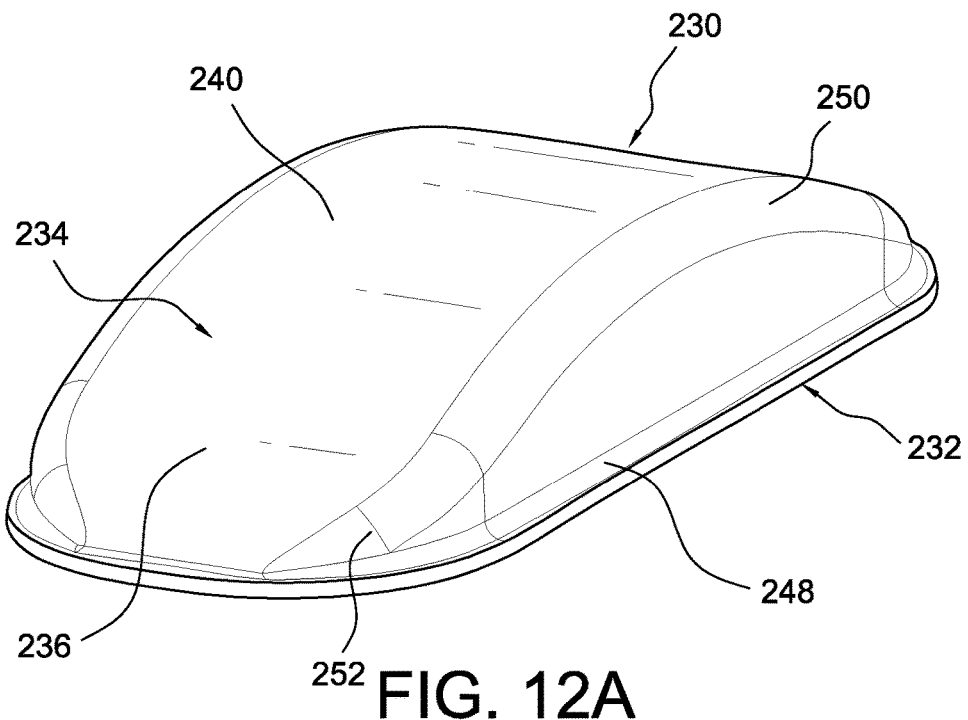
FIG. 12A is a perspective view of a tibia pad for use in the orthopedic device.

FIG. 12A shows an embodiment of the tibia pad 230 adapted for both right and left legs, and is adapted in combination with the lower frame component, as shown in FIGS. 10 and 11. The tibial pad 230 includes a substantially flat first surface 232 bounded by first and second ends 236, 238 of the tibia pad 230. A profile 242 of the first surface 232 is generally adapted to a contour of the tibia of a user. The tibia pad 230 has a rounded second surface 234 having a profile 240 generally corresponding to the inner contour of the center section 140 of the second frame component 114.

Figure 12B:
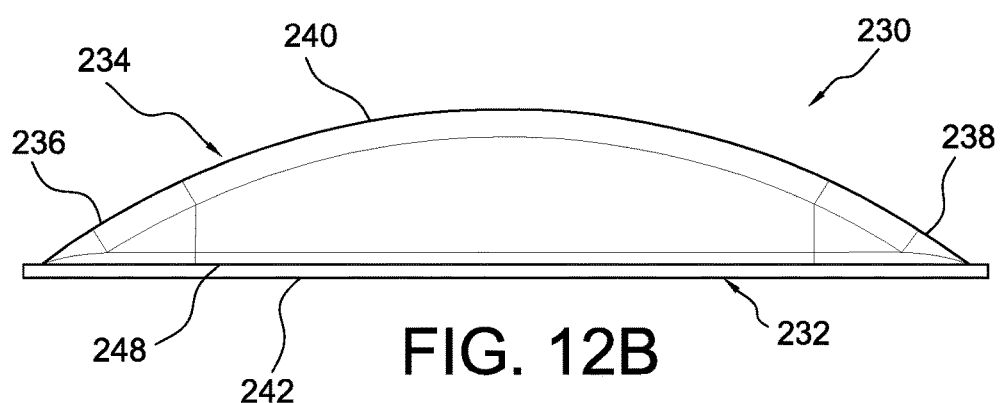
FIG. 12B is an elevational view of the tibia pad of FIG. 9.

FIGS. 12A and 12B show the tibia pad 230 as being preferably symmetric in shape from the first and second ends 236, 238 so as to accommodate either direction the tibia pad 230 is placed along the second frame component. As shown in the contoured configurations of the orthopedic device, the center section of the second frame component has a curvature as it extends between the first and second sections corresponding to lateral and medial sides of the orthopedic device and leg of the user. The tibia pad is configured and dimensioned to fit at a plurality of locations along the curvature of the second frame component.

The first surface 232 extends from a base portion 248 which assures a substantially flat surface from which the second surface 234 rises. To relieve any stress points and minimize discomfort, the tibia pad 230 includes tapering ends 252 which meet the first and second ends 236, 238 and merges with the base portion 248 in a graduated manner, and filleted side haunches 250. The tapering ends 252 and filleted side haunches 250 ease donning of the brace, and prevent interference with any clothing, skin and hair along the leg.

The tibia pad 230 may be formed from a variety of padding materials. The tibia pad may be formed from ethylene vinyl acetate (EVA) type foam cut to shape, and having compressible properties, yet having sufficient rigidity. The rigidity supports against the leg and accommodates the void created by the generally uniform profile of the second frame component on the medial side of the orthopedic device against the tibia, for either left or right sided applications.

The tibia pad 230 may be secured to the frame component permanently or temporarily, or alternatively may be secured to the liner. The tibia pad may include hook material, and the frame component or the liner may include a loop material to which the hook material secures. Alternatively, the tibia pad may adhere to the frame component with an adhesive or other known fastener means.

Figure 13:
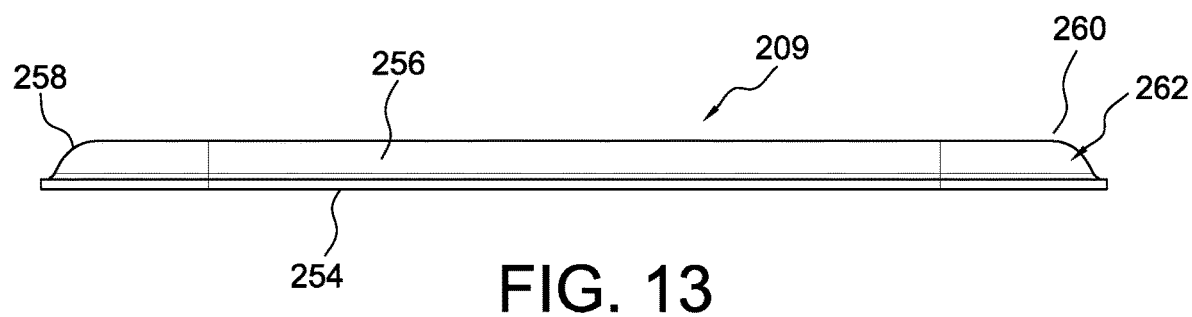
FIG. 13 is an elevational view of a tibia strap pad of the orthopedic device.

FIG. 13 depicts a strap pad 209 arranged along the tibia strap 207 in FIG. 8. The tibia strap 209 in FIG. 8 should extend between the hinge assemblies and can be adjustably lengthened according to desired tension, and the strap pad 209 is preferably dimensioned and configured to fit within a distance between hinge assemblies on lateral and medial sides of the orthopedic device.

A first surface 254 of the strap pad 209 is substantially flat and should face the leg of the wearer. A second surface 256 of the strap pad 209 is spaced from the first surface 254, and a curved profile 262 extends from between the first and second surfaces 254, 256, and first and second ends 258, 260 to provide a gentle taper of the strap pad 209 and improve cushioning. The strap pad 209 may be removably mounted to tibia strap 207 depending on the level of cushioning desired by the user.

It is to be understood that not necessarily all objects or advantages may be achieved under any embodiment of the disclosure. Those skilled in the art will recognize that the orthopedic device may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to construct an orthopedic device under principles of the present disclosure. It will be understood by the skilled artisan that the features described may be adapted to other types of orthopedic devices. Hence this disclosure and the embodiments and variations thereof are not limited to knee braces, but can be utilized in any orthopedic devices.

Although this disclosure describes certain exemplary embodiments and examples of an orthopedic device, it therefore will be understood by those skilled in the art that the present disclosure extends beyond the specifically disclosed knee brace embodiments to other alternative embodiments and/or uses of the disclosure and obvious modifications and equivalents thereof. It is intended that the present disclosure should not be limited by the particular disclosed embodiments described above, and may be extended to orthopedic devices and supports, and other applications that may employ the features described.

The invention claimed is:

1. A strap kit for securing to a frame of an orthopedic device, the frame having first and second components connected to one another by a hinge assembly, and each of the first and second frame components also having first and second sides opposed to one another and defined on one of lateral and medial sides, the strap kit comprising:
    a first strap having first and second ends, the first strap further having a first hook element located at one of said first and second ends;
    a first subshell arranged for securing to the second side of the first frame component, the first subshell having a first end arranged to extend laterally, at least in part, beyond the first frame component, the first subshell adapted to flex relative to the first frame component and mount to an inside surface of the first frame component, the first subshell defining a keyhole arranged for receiving the first hook element;
    wherein the first strap is arranged to spiral from the first frame component to the second frame component between the first and second sides of the frame.

2. The strap kit of claim 1, wherein the first subshell is contoured with corresponding structure of the frame.

3. The strap kit of claim 2, wherein the first subshell defines a plurality of protrusions arranged to correspond in shape and size to a plurality of openings defined by the frame.

4. The strap kit of claim 1, further comprising at least one fastener arranged to extend through an opening defined by the first subshell and couple to the frame.

5. The strap kit of claim 1, wherein the first subshell defines an aperture adapted for passage of a fastener for coupling the first subshell to the frame.

6. The strap kit of claim 1, wherein the first subshell defines a slot for receiving a second strap extending from a first side of the frame, the first subshell securable to a second side of the frame.

7. The strap kit of claim 1, wherein the keyhole of the first subshell defines a larger portion for receiving the hook element of the first strap, and a smaller portion continuous with the larger portion and for locking the hook element with the first subshell.

8. The strap kit of claim 7, wherein a reinforcing edge is formed about at least the smaller portion to reinforce the first subshell.

9. A strap kit for securing to a frame of an orthopedic device, the frame having first and second components connected to one another by a hinge assembly, and each of the first and second frame components also having first and second sides opposed to one another and defined on one of lateral and medial sides, the strap kit comprising:
    a first strap having first and second ends, the first strap further having a first hook element located at one of said first and second ends;
    a first subshell arranged for securing to the second side of the first frame component, the first subshell having a first end arranged to extend laterally, at least in part, beyond the first frame component, the first subshell adapted to flex relative to the first frame component and mount to an inside surface of the first frame component, the first subshell defining a keyhole arranged for receiving the first hook element;
    second subshell arranged for securing to the second end at a second side of the frame, a second end of the first strap securing to the second subshell.

10. The strap kit of claim 9, further comprising a buckle assembly securable to the second subshell, the buckle assembly having a lateral portion and an angled portion oriented relative to the lateral portion, the second end of the first strap arranged to secure to the angled portion, and a third strap is securable to the second side of the frame and to the lateral portion of the buckle assembly.

11. The strap kit of claim 9, wherein the second subshell defines locking elements adapted to interlock with the second side at the second end of the frame.

12. The strap kit of claim 9, wherein the first strap is arranged to spiral between the first and second subshells from the first end of the frame to the second end of the frame between the first and second sides of the frame.

13. The strap kit of claim 9, wherein the first and second subshells are more flexible than the frame.

14. An orthopedic device, comprising:
- a frame including a first frame component defining first and second extensions and a center section spanning between the first and second extensions;
- a second frame component defining first and second extensions and a center section spanning between the first and second extensions, the second frame component defining a flattened region located between the center section and one of the first or second extensions, an opposing side of the center section of the second frame component is devoid of the flattened region, the center section having a uniform height and corners defined between the center section and the first and second extensions are symmetrical;
- a hinge assembly including first and second hinges or joints connecting the first and second frame components by the first and second extensions of the first and second frame components;
- a tibial pad having a same height as the center section and arranged to extend along an inner surface of the second frame component, the tibial pad having a first surface forming a substantially flat profile bounded by first and second ends, the substantially flat profile adapted to a contour of a tibia of a user, the tibial pad having a second surface opposite the first surface generally corresponding to an inner contour of the center section of the second frame component;
- a liner arranged along the tibial pad and a remainder of the second frame component outside of the tibial pad, the liner being pliable and conforming to a shape of the second frame component and the tibial pad.

15. An orthopedic device, comprising:
- a frame including a first frame component defining first and second extensions at first and second sides of the first frame component, and a center section spanning between the first and second extensions; a second frame component defining first and second extensions at first and second sides of the second frame component, and a center section spanning between the first and second extensions; and a hinge assembly including first and second hinges or joints connecting the first and second frame components by the first and second extensions of the first and second frame components;
- a first strap having first and second ends, the first strap further having a first hook element located at one of said first and second ends;
- a first subshell arranged for securing to the first end at the second side of the first frame component, the first subshell having a first end arranged to extend laterally, at least in part, beyond the first side of the first frame component, the first sub shell adapted to flex relative to the first frame component and mount to an inside surface of the first frame component, the first subshell defining a keyhole arranged for receiving the first hook element.

16. The orthopedic device of claim 15, further comprising a second subshell arranged for securing to the second end at a first side of the frame, a second end of the first strap securing to the second subshell.

17. The orthopedic device of claim 16, further comprising a buckle assembly securable to the second subshell, the buckle assembly having a lateral portion and an angled portion oriented relative to the lateral portion, the second end of the first strap arranged to secure to the angled portion, and a third strap is securable to the second side of the frame and to the lateral portion of the buckle assembly.

18. The orthopedic device of claim 16, wherein the first and second subshells are contoured with corresponding structure of the frame.

19. The orthopedic device of claim 16, wherein the first strap is arranged to spiral between the first and second subshells from the first end of the frame to the second end of the frame between the first and second sides of the frame.

* * * * *